(12) United States Patent
Fuchs et al.

(10) Patent No.: US 6,509,019 B1
(45) Date of Patent: Jan. 21, 2003

(54) **IMMUNOLOGICALLY ACTIVE PROTEINS FROM *BORRELIA BURGDORFERI***

(75) Inventors: Renate Fuchs, Deisenhofen (DE); Bettina Wilske, München (DE); Vera Preac-Mursic, München (DE); Manfred Motz, München (DE); Erwin Soutscheck, München (DE)

(73) Assignee: Mikrogen Molekularbiologische Entwicklungs-GmbH, Munich (DE)

( * ) Notice: Subject to any disclaimer, the term of this patent is extended or adjusted under 35 U.S.C. 154(b) by 0 days.

(21) Appl. No.: 09/711,546

(22) Filed: Nov. 13, 2000

Related U.S. Application Data

(62) Division of application No. 08/209,603, filed on Mar. 10, 1994, now Pat. No. 6,248,538, which is a continuation of application No. 07/862,535, filed on Jun. 19, 1992, now abandoned.

(30) Foreign Application Priority Data

Dec. 22, 1989 (DE) ......................................... 39 42 728
Jun. 13, 1990 (DE) ......................................... 40 18 988

(51) Int. Cl.⁷ ........................ A61K 39/02; A61K 38/00; C07K 14/00; C07K 1/00
(52) U.S. Cl. ............................... 424/190.1; 424/234.1; 530/300; 530/350
(58) Field of Search ................................. 530/300, 350; 424/190.1, 234.1

(56) References Cited

U.S. PATENT DOCUMENTS 4,888,276 A    12/1989    Shelburne
5,620,862 A     4/1997    Padula

OTHER PUBLICATIONS

*Antibodies, A Laboratory Manual*, Harlow and Lane (ed), 342, 343, 560–562, 5, (1988).

Barbour, A.G., "Plasmid Analysis of Borrelia Burgdorferi, the Lyme Disease Agent", *Journal of Clinical Microbiology*, 26, 475–478, (Mar. 1988).

Barbour, A.G., et al., "Lyme Disease Spirochetes and Ixodid Tick Spirochetes Share a Common Surface Antigenic Determinant Defined by a Monoclonal Antibody", *Infection and Immunity*, 41, 795–804, (Aug. 1983).

Berzofsky, J.A., "Intrinsic and Extrinsic Factors in Protein Antigenic Structure", *Science*, 229, 932–940, (1985).

Bowie, et al., "Deciphering the Message in Protein Sequences: Tolerance to Amino Acid Substitutions", *Science*, 247, 1306–1310, (Mar. 1990).

Gassmann, G.S., et al., "Nucleotide Sequence of a Gene Encoding the Borrelia burgdorferi flagellin", *Nucleic Acids Research*, 17, 3590, (1989).

Hansen, K., et al., "Measurement of Antibodies to the Borrelia burgdorferi Flagellum Improves Serodiagnosis in Lyme Disease", *Journal of Clinical Microbiology*, 26, 338–346, (Feb. 1988).

Hinnesbusch, J., et al., "Linear–and Circular–Plasmid Copy Numbers in Borrelia Burgdorferi", *Journal of Bacteriology*, 174, 5251–5257, (Aug. 1992).

Hopp, et al., "Prediction of Protein Antigenic Determinants from Amino Acid Sequences", *Proceedings of National Academy of Sciences, USA* 78, 3824–3828, (1981).

Hyde, F.W., et al., "Detection of Antigens in Urine of Mice and Humans Infected with Borrelia burgdorferi, Etiologic Agent of Lyme Disease", *Journal of Clinical Microbiology*, 58–61, (1989).

Kumar, et al., *PNAS*, 87, 1337–1341, (Feb. 1990).

Pennell, et al., "An Indirect Quantitative Fluorescence Immunoassay for the Detection of Lyme Disease Serum Antibody", *Annals of the NY Academy of Sciences*, 539, 483–484, (1988).

Preac–Mursic, V., et al., "European Borrelia burgdorferi Isolated from Humans and Ticks–Culture Conditions and Antibiotic Susceptibility", *Zbl. Bakt. Hyg.*, A263, 112–118, (1986).

Sadziene, A., et al., "The Cryptic ospC Gene of Borrelia burgdorferi B31 is located on a circular plasmid", *Infection and Immunity*, 61, 5, 2192–2195, (1993).

Simon, et al., "Recombinant Outer Surface Protein A from Borrelia burgdorferi Induces Antibodies Protective against pirochetal Infection in Mice", *Journal of Infectious Diseases*, 164, 123–132, (Jul. 1991).

Stern, P.S., "Predicting Antigenic Sites on Proteins", *TIBTECH*, 9, 163–167, (May, 1991).

(List continued on next page.)

*Primary Examiner*—Mark Navarro
(74) *Attorney, Agent, or Firm*—Schwegman, Lundberg, Woessner & Kluth, P.A.

(57) ABSTRACT

Various immunologically active proteins from *Borrelia burgdorferi* have been prepared by genetic manipulation in microorganisms. To do this, the specific DNA sequences were selected from a *B. burgdorferi* gene bank using suitable screening methods, or were prepared directly by DNA amplification using selected hybridization probes, and were placed under the control of inducible promoters such as, for example, the lac promoter. It has been possible, owing to description of efficient purification methods for the expressed antigens, to provide the proteins in a suitable way. These proteins can be used to produce specific and sensitive diagnostic assay kits. The specific combination of the immunologically active proteins makes precise diagnosis possible. Furthermore, monoclonal antibodies have been generated and are used as reagents for detecting pathogens directly in test samples or after cultivation. The *Borrelia burgdorferi*-specific DNA sequences can be employed for direct detection of the pathogen in patients' samples (for example by means of the PCR reaction).

5 Claims, 9 Drawing Sheets

OTHER PUBLICATIONS

Wallich, R., et al., "Clonign and Sequencing of the Gene Encoding the Outer Surface Protein A (OspA) of a European Borrelia burgdorferi isolate", *Nucleic Acids Research*, 17, 8864, (Nov. 1989).

Wilske, et al., "Antigenic Variability of Borrelia burgdorferi", *Annals of the New York Academy of Sciences*, 539, 126–143, (Aug. 1988).

Wilske, et al., "Immunochemical Analysis of the Immune Response in Late Manifestations of Lyme Borreliosis", *Zbl. Bakt. Hyg*, A 267, 549–558, (1988).

Wilske, et al., "Immunochemical and Immunological Analysis of European Borrelia burgdorferi Strains", *International Journal of Microbiology and Hygiene*, 263, Series A, 92–102, (1986).

Young, et al., "Efficient Isolation of Genes by Using Antibody Probes", *Proceedings of National Academy of Sciences, USA* 80, 1194–1198, (1983).

Plotkin et al (ed.) *Vaccines* W.B. Saunders Co. Philadelphia p. 571, 1988.*

* cited by examiner

IgG WESTERN BLOT WITH 5 DIFFERENT STRAINS AS ANTIGEN
IgG AND IgM RESPONSE IN STAGE II
IgG RESPONSE IN STAGE III

NEUROBORRELIOSIS, STAGE II
(IgM)　　　　　(IgG)

Neuroborreliose, Stadium II
(IgM)　　　　　(IgG)

p41
pC

Acrodermatitis　　Arthritis
(IgG)　　　　　(IgG)

p100
p60
p41
p17 p100
p60
p41
OspA
OspB
pC

FIG. 1

MONOCLONAL ANTIBODIES AGAINST B. BURGDORFERI

FIG. 7a

SEQUENCE LISTING

```
<160> NUMBER OF SEQ ID NOS:  16

<210> SEQ ID NO 1
<211> LENGTH: 39
<212> TYPE: DNA
<213> ORGANISM: Borrelia burgdorferi

<400> SEQUENCE: 1
atgaccatga ttacgaattc ccgggatcc atcatgatt                            39

<210> SEQ ID NO 2
<211> LENGTH: 20
<212> TYPE: PRT
<213> ORGANISM: Borrelia burgdorferi

<400> SEQUENCE: 2

Glu Leu Asp Lys Glu Lys Leu Lys Asp Phe Val Asn Leu Asp Leu Glu
 1               5                  10                  15

Phe Val Asn Thr
         20

<210> SEQ ID NO 3
<211> LENGTH: 61
<212> TYPE: DNA
<213> ORGANISM: Borrelia burgdorferi

<400> SEQUENCE: 3
garytdgaya argaraaryt daargaytty gtwaayytdg ayyadgartt ygtwaaytay    60
a                                                                    61

<210> SEQ ID NO 4
<211> LENGTH: 346
<212> TYPE: DNA
<213> ORGANISM: Borrelia burgdorferi

<400> SEQUENCE: 4
atgaaaaaaa tgttactaat ctttagtttt tttcttgttt ttttaaatgg atttcctctt    60
aatgcaaggg aagttgataa ggaaaaatta aaggactttg ttaatatgga tcttgaattt  120
gttaattaca aggtcctta tgattctaca aatacatatg aacaaatagt aggtattggg  180
gagtttttag caaggccgtt gatcaattcc aatagtaagt caagttatta tggtaaatat  240
tttgttaata gatttattga cgatcaagat aaaaaagcaa gtgttgatat tttttctatt  300
ggtagtaagt cagagcttga tagtatatta aatctaagaa gaattc                  346

<210> SEQ ID NO 5
<211> LENGTH: 663
<212> TYPE: PRT
<213> ORGANISM: Borrelia burgdorferi

<400> SEQUENCE: 5
```

```
Met Lys Lys Met Leu Leu Ile Phe Ser Phe Phe Leu Val Phe Leu Asn
 1               5                  10                 15
Gly Phe Pro Leu Asn Ala Arg Glu Val Asp Lys Glu Lys Leu Lys Asp
             20                  25                  30
Phe Val Asn Met Asp Leu Glu Phe Val Asn Tyr Lys Gly Pro Tyr Asp
             35                  40                  45
Ser Thr Asn Thr Tyr Glu Gln Ile Val Gly Ile Gly Glu Phe Leu Ala
 50                  55                  60
Arg Pro Leu Ile Asn Ser Asn Ser Asn Ser Ser Tyr Tyr Gly Lys Tyr
 65              70                  75                  80
Phe Val Asn Arg Phe Ile Asp Asp Gln Asp Lys Lys Ala Ser Val Asp
             85                  90                  95
Ile Phe Ser Ile Gly Ser Lys Ser Glu Leu Asp Ser Ile Leu Asn Leu
            100                 105                 110
Arg Arg Ile Leu Thr Gly Tyr Leu Ile Lys Ser Phe Asp Tyr Glu Arg
            115                 120                 125
Ser Ser Ala Glu Leu Ile Ala Lys Ala Ile Thr Ile Tyr Asn Ala Val
130                 135                 140
Tyr Arg Gly Asp Leu Asp Tyr Tyr Lys Glu Phe Tyr Ile Glu Ala Ser
145             150                 155                 160
Leu Lys Ser Leu Thr Lys Glu Asn Ala Gly Leu Ser Arg Val Tyr Ser
                165                 170                 175
Gln Trp Ala Gly Lys Thr Gln Ile Phe Ile Pro Leu Lys Lys Asn Ile
            180                 185                 190
Leu Ser Gly Asn Val Glu Ser Asp Ile Asp Ile Asp Ser Leu Val Thr
            195                 200                 205
Asp Lys Val Ala Ala Leu Leu Ser Glu Asn Glu Ser Gly Val Asn
210                 215                 220
Phe Ala Arg Asp Ile Thr Asp Ile Gln Gly Glu Thr His Lys Ala Asp
225                 230                 235                 240
Gln Asp Lys Ile Asp Ile Glu Leu Asp Asn Phe His Glu Ser Asp Ser
                245                 250                 255
Asn Ile Thr Glu Thr Ile Glu Asn Leu Arg Asp Gln Leu Glu Lys Ala
            260                 265                 270
Thr Asp Glu Glu His Lys Lys Glu Ile Glu Ser Gln Val Asp Ala Lys
        275                 280                 285
Lys Lys Gln Lys Glu Glu Leu Asp Lys Lys Ala Ile Asp Leu Asp Lys
        290                 295                 300
Ala Gln Gln Lys Leu Asp Phe Ala Glu Asp Asn Leu Asp Ile Gln Arg
305                 310                 315                 320
Asp Thr Val Arg Glu Lys Leu Gln Glu Asn Ile Asn Glu Thr Asn Lys
                325                 330                 335
Glu Lys Asn Leu Pro Lys Pro Gly Asp Val Ser Ser Pro Lys Val Asp
            340                 345                 350
Lys Gln Leu Gln Ile Lys Glu Ser Leu Glu Asp Leu Gln Glu Gln Leu
        355                 360                 365
Lys Glu Ala Ser Asp Glu Asn Gln Lys Arg Glu Ile Glu Lys Gln Ile
        370                 375                 380
Glu Ile Lys Lys Asn Asp Glu Glu Leu Phe Lys Asn Lys Asp His Lys
385                 390                 395                 400
Ala Leu Asp Leu Lys Gln Glu Leu Asn Ser Lys Ala Ser Ser Lys Glu
            405                 410                 415
```

Lys Ile Glu Gly Glu Glu Asp Lys Glu Leu Asp Ser Lys Lys Asn
            420                 425                 430

Leu Glu Pro Val Ser Glu Ala Asp Lys Val Asp Lys Ile Ser Lys Ser
            435                 440                 445

Asn Asn Asn Glu Val Ser Lys Leu Ser Pro Leu Asp Glu Pro Ser Tyr
            450                 455                 460

Ser Asp Ile Asp Ser Lys Glu Gly Val Asp Asn Lys Asp Val Asp Leu
465                 470                 475                 480

Gln Lys Thr Lys Pro Gln Val Glu Ser Gln Pro Thr Ser Leu Asn Glu
            485                 490                 495

Asp Leu Ile Asp Val Ser Ile Asp Ser Ser Asn Pro Val Phe Leu Glu
            500                 505                 510

Val Ile Asp Pro Ile Thr Asn Leu Gly Thr Leu Gln Leu Ile Asp Leu
            515                 520                 525

Asn Thr Gly Val Arg Leu Lys Glu Ser Ala Gln Gln Gly Ile Gln Arg
            530                 535                 540

Tyr Gly Ile Tyr Glu Arg Glu Lys Asp Leu Val Val Ile Lys Ile Asp
545                 550                 555                 560

Ser Gly Lys Ala Lys Leu Gln Ile Leu Asp Lys Leu Glu Asn Leu Lys
            565                 570                 575

Val Ile Ser Glu Ser Asn Phe Glu Ile Asn Lys Asn Ser Ser Leu Tyr
            580                 585                 590

Val Asp Ser Arg Met Ile Leu Val Val Lys Asp Asp Ser Asn Ala
            595                 600                 605

Trp Arg Leu Ala Lys Phe Ser Pro Lys Asn Leu Asp Glu Phe Ile Leu
            610                 615                 620

Ser Glu Asn Lys Ile Leu Pro Phe Thr Ser Phe Ala Val Arg Lys Asn
625                 630                 635                 640

Phe Ile Tyr Leu Gln Asp Glu Leu Lys Ser Leu Val Thr Leu Asp Val
            645                 650                 655

Asn Thr Leu Lys Lys Val Lys
            660

<210> SEQ ID NO 6
<211> LENGTH: 13
<212> TYPE: PRT
<213> ORGANISM: Borrelia burgdorferi

<400> SEQUENCE: 6

Lys Ile Thr Asp Ser Asn Ala Thr Val Leu Ala Val Lys
1               5                   10

<210> SEQ ID NO 7
<211> LENGTH: 11
<212> TYPE: PRT
<213> ORGANISM: Borrelia burgdorferi

<400> SEQUENCE: 7

Asp Leu Phe Glu Ser Val Glu Gly Leu Leu Lys
1               5                   10

<210> SEQ ID NO 8
<211> LENGTH: 40
<212> TYPE: DNA
<213> ORGANISM: Borrelia burgdorferi

<400> SEQUENCE: 8
aaratwacwg aywcwaaygc wacwgtwytd gcwgtwaara                              40

<210> SEQ ID NO 9
<211> LENGTH: 34
<212> TYPE: DNA
<213> ORGANISM: Borrelia burgdorferi

<400> SEQUENCE: 9
gayytdttyg arwcwgtwga rgghytdytd aara                                  34

<210> SEQ ID NO 10
<211> LENGTH: 639
<212> TYPE: DNA
<213> ORGANISM: Borrelia burgdorferi

<400> SEQUENCE: 10
atgaaaaaga atacattaag tgcgatatta atgactttat ttttatttat atcttgtaat      60
aattcaggga aggtggggat tctgcatcta ctaatcctgc tgacgagtct tgcgaaaggg     120
cctaatctta cagaaataag caaaaaaatt acagattcta atgcatttgt acttgctgtt    180
aaagaagttg agactttggt tttatctata gatgaacttg ctaagaaagc tattggtcaa    240
aaaatagaca ataataatgg tttagctgct ttaaataatc agaatggatc gttgttagca    300
ggagcctatg caatatcaac cctaataaca gaaaaattga gtaaattgaa aaatttagaa    360
gaattaaaga cagaaattgc aaaggctaag aaatgttccg aagaatttac taataaacta    420
aaaagtggtc atgcagatct tggcaaacag gatgctaccg atgatcatgc aaaagcagct    480 atttttaaaaa cacatgcaac taccgataaa ggtgctaaag aatttaaaga tttatttgaa    540
tcagtagaag gtttgttaaa agcagctcaa gtagcactaa ctaattcagt taaagaactt    600
acaagtcctg ttgtagcaga aagtccaaaa aaaccttaa                            639

<210> SEQ ID NO 11
<211> LENGTH: 212
<212> TYPE: PRT
<213> ORGANISM: Borrelia burgdorferi

<400> SEQUENCE: 11

Met Lys Lys Asn Thr Leu Thr Ala Ile Leu Met Thr Leu Phe Leu Phe
1               5                   10                  15

Ile Ser Cys Asn Asn Ser Gly Lys Val Gly Ile Leu Thr Ser Thr Asn
            20                  25                  30

Pro Ala Asp Glu Ser Ala Lys Gly Pro Asn Leu Thr Glu Ile Ser Lys
        35                  40                  45

Lys Ile Thr Asp Ser Asn Ala Phe Val Leu Ala Val Lys Glu Val Glu
    50                  55                  60

Thr Leu Val Leu Ser Ile Asp Glu Leu Ala Lys Lys Ala Ile Gly Gln
65                  70                  75                  80

Lys Ile Asp Asn Asn Asn Gly Leu Ala Ala Leu Asn Asn Gln Asn Gly
                85                  90                  95

Ser Leu Leu Ala Gly Ala Tyr Ala Ile Ser Thr Leu Ile Thr Glu Lys
            100                 105                 110

Leu Ser Lys Leu Lys Asn Leu Glu Glu Leu Lys Thr Glu Ile Ala Lys
        115                 120                 125

Ala Lys Lys Cys Ser Glu Glu Phe Thr Asn Lys Leu Lys Ser Gly His
    130                 135                 140

Ala Asp Leu Gly Lys Gln Asp Ala Thr Asp Asp His Ala Lys Ala Ala
145                 150                 155                 160

```
Ile Leu Lys Thr His Ala Thr Thr Asp Lys Gly Ala Lys Glu Phe Lys
                165                 170                 175

Asp Leu Phe Glu Ser Val Glu Gly Leu Leu Lys Ala Ala Gln Val Ala
            180                 185                 190

Leu Thr Asn Ser Val Lys Glu Leu Thr Ser Pro Val Ala Glu Ser
        195                 200                 205

Pro Lys Lys Pro
    210

<210> SEQ ID NO 12
<211> LENGTH: 680
<212> TYPE: DNA
<213> ORGANISM: Borrelia burgdorferi

<400> SEQUENCE: 12
atgaaaaaat atttattggg aataggtcta atattagcct taatagcatg caagcaaaat      60
gttagcagcc ttgatgaaaa aaacagcgct tcagtagatt tgcctggtga gatgaaagtt    120
cttgtaagta agaaaaaaga caaagacggt aagtacagtc taaaggcaac agtagacaag    180
attgagctaa aggaacttc tgataaagac aatggttctg gggtgcttga aggtacaaaa     240
gatgacaaaa gtaaagcaaa attaacaatt gctgacgatc taagtaaaac cacattcgaa    300
cttttcaaag aagatggcaa acattagtg tcaagaaaag taagttctaa agacaaaaca     360
tcaacagatg aaatgttcaa tgaaaaaggt gaattgtctg caaaaaccat gacaagagaa    420
aatggaacca aacttgaata tacagaaatg aaaagcgatg gaaccggaaa agctaaagaa    480
gttttaaaaa actttactct tgaaggaaaa gtagctaatg ataaagtaac attggaagta    540
aaagaaggaa ccgttacttt aagtaaggaa attgcaaaat ctggagaagt aacagttgct    600
cttaatgaca ctaacactac tcaggctact aaaaaaactg gcgcatggga ttcaaaaact    660
tctactttaa caattagtgt                                                680

<210> SEQ ID NO 13
<211> LENGTH: 273
<212> TYPE: PRT
<213> ORGANISM: Borrelia burgdorferi

<400> SEQUENCE: 13

Met Lys Lys Tyr Leu Leu Gly Ile Gly Leu Ile Leu Ala Leu Ile Ala
  1               5                  10                  15

Cys Lys Gln Asn Val Ser Ser Leu Asp Glu Lys Asn Ser Ala Ser Val
                 20                  25                  30

Asp Leu Pro Gly Glu Met Lys Val Leu Val Ser Lys Glu Lys Asp Lys
             35                  40                  45

Asp Gly Lys Tyr Ser Leu Lys Ala Thr Val Asp Lys Ile Glu Leu Lys
         50                  55                  60

Gly Thr Ser Asp Lys Asp Asn Gly Ser Gly Val Leu Glu Gly Thr Lys
 65                  70                  75                  80

Asp Asp Lys Ser Lys Ala Lys Leu Thr Ile Ala Asp Leu Ser Lys
                 85                  90                  95

Thr Thr Phe Glu Leu Phe Lys Glu Asp Gly Lys Thr Leu Val Ser Arg
                100                 105                 110

Lys Val Ser Ser Lys Asp Lys Thr Ser Thr Asp Glu Met Phe Asn Glu
            115                 120                 125

Lys Gly Glu Leu Ser Ala Lys Thr Met Thr Arg Glu Asn Gly Thr Lys
        130                 135                 140
```

```
Leu Glu Tyr Thr Glu Met Lys Ser Asp Gly Thr Gly Lys Ala Lys Glu
145                 150                 155                 160

Val Leu Lys Asn Phe Thr Leu Glu Gly Lys Val Ala Asn Asp Lys Val
                165                 170                 175

Thr Leu Glu Val Lys Glu Gly Thr Val Thr Leu Ser Lys Glu Ile Ala
            180                 185                 190

Lys Ser Gly Glu Val Thr Val Ala Leu Asn Asp Thr Asn Thr Thr Gln
        195                 200                 205

Ala Thr Lys Lys Thr Gly Ala Trp Asp Ser Lys Thr Ser Thr Leu Thr
    210                 215                 220

Ile Ser Val Asn Ser Lys Lys Thr Thr Gln Leu Val Phe Thr Lys Gln
225                 230                 235                 240

Asp Thr Ile Thr Val Gln Lys Tyr Asp Ser Ala Gly Thr Asn Leu Glu
                245                 250                 255

Gly Thr Ala Val Glu Ile Lys Ser Leu Asp Glu Leu Lys Asn Ala Leu
            260                 265                 270

Lys
```

<210> SEQ ID NO 14
<211> LENGTH: 341
<212> TYPE: PRT
<213> ORGANISM: Borrelia burgdorferi

<400> SEQUENCE: 14

```
Met Arg Gly Ser Ile Met Ile Ile Asn His Asn Thr Ser Ala Ile Asn
1               5                   10                  15

Ala Ser Arg Asn Asn Ala Ile Asn Ala Ala Asn Leu Ser Lys Thr Gln
            20                  25                  30

Glu Lys Leu Ser Ser Asn Tyr Arg Ile Asn Arg Ala Ser Asp Asp Ala
        35                  40                  45

Ala Gly Met Gly Val Ser Gly Lys Ile Asn Ala Gln Ile Arg Gly Leu
    50                  55                  60

Ser Gln Ala Ser Arg Asn Thr Ser Lys Ala Ile Asn Phe Ile Gln Thr
65                  70                  75                  80

Thr Glu Gly Asn Leu Asn Glu Val Glu Lys Val Leu Val Arg Met Lys
                85                  90                  95

Glu Leu Ala Val Gln Ser Gly Asn Gly Thr Tyr Ser Asp Ser Asp Arg
            100                 105                 110

Gly Ser Ile Gln Ile Glu Ile Glu Gln Leu Thr Asp Glu Ile Asn Arg
        115                 120                 125

Ile Ala Asp Gln Ala Gln Tyr Asn Gln Met His Met Leu Ser Asn Lys
    130                 135                 140

Ser Ala Ser Gln Asn Val Lys Thr Ala Glu Glu Leu Gly Met Gln Pro
145                 150                 155                 160

Ala Lys Ile Asn Thr Pro Ala Ser Leu Ser Gly Ser Gln Ala Ser Trp
                165                 170                 175

Thr Leu Arg Val His Val Gly Ala Asn Gln Asp Glu Ala Ile Ala Val
            180                 185                 190

Asn Ile Tyr Ser Ala Asn Val Ala Asn Leu Phe Ala Gly Glu Gly Ala
        195                 200                 205

Gln Ala Ala Gln Ala Ala Pro Val Gln Glu Gly Ala Gln Glu Glu Gly
    210                 215                 220

Ala Gln Gln Pro Thr Pro Ala Thr Ala Pro Thr Gln Gly Gly Val Asn
225                 230                 235                 240
```

-continued

```
Ser Pro Val Asn Val Thr Thr Val Asp Ala Asn Thr Ser Leu Ala
            245                 250                 255

Lys Ile Glu Asn Ala Ile Arg Met Ile Ser Asp Gln Arg Ala Asn Leu
        260                 265                 270

Gly Ala Phe Gln Asn Arg Leu Glu Ser Ile Lys Asn Ser Thr Glu Tyr
            275                 280                 285

Ala Ile Glu Asn Leu Lys Ala Ser Tyr Ala Gln Ile Lys Asp Ala Thr
        290                 295                 300

Met Thr Asp Glu Val Val Ala Ala Thr Thr Asn Ser Ile Leu Thr Gln
305                 310                 315                 320

Ser Ala Met Ala Met Ile Ala Gln Ala Asn Gln Val Pro Gln Tyr Val
                325                 330                 335

Leu Ser Leu Leu Arg
            340

<210> SEQ ID NO 15
<211> LENGTH: 209
<212> TYPE: PRT
<213> ORGANISM: Borrelia burgdorferi

<400> SEQUENCE: 15

Met Lys Lys Asn Thr Leu Ser Ala Ile Leu Met Thr Leu Phe Leu Phe
1               5                   10                  15

Ile Ser Cys Asn Asn Ser Gly Lys Asp Gly Asn Thr Ser Ala Asn Ser
            20                  25                  30

Ala Asp Glu Ser Val Lys Gly Pro Asn Leu Thr Glu Ile Ser Lys Lys
        35                  40                  45

Ile Thr Asp Ser Asn Ala Val Leu Leu Ala Val Lys Glu Val Glu Ala
    50                  55                  60

Leu Leu Ser Ser Ile Asp Glu Ile Ala Ala Lys Ala Ile Gly Lys Lys
65                  70                  75                  80

Ile His Gln Asn Asn Gly Leu Asp Thr Glu Asn Asn His Asn Gly Ser
                85                  90                  95

Leu Leu Ala Gly Ala Tyr Ala Ile Ser Thr Leu Ile Lys Gln Lys Leu
            100                 105                 110

Asp Gly Leu Lys Asn Glu Gly Leu Lys Glu Lys Ile Asp Ala Ala Lys
        115                 120                 125

Lys Cys Ser Glu Thr Phe Thr Asn Lys Leu Lys Glu Lys His Thr Asp
    130                 135                 140

Leu Gly Lys Glu Gly Val Thr Asp Ala Asp Ala Lys Glu Ala Ile Leu
145                 150                 155                 160

Lys Thr Asn Gly Thr Lys Thr Lys Gly Ala Glu Glu Leu Gly Lys Leu
                165                 170                 175

Phe Glu Ser Val Glu Val Leu Ser Lys Ala Ala Lys Glu Met Leu Ala
            180                 185                 190

Asn Ser Val Lys Glu Leu Thr Ser Pro Val Val Ala Glu Ser Pro Lys
        195                 200                 205

Pro

<210> SEQ ID NO 16
<211> LENGTH: 13
<212> TYPE: PRT
<213> ORGANISM: Borrelia burgdorferi
```

```
<400> SEQUENCE: 16

Met Thr Met Ile Thr Asn Ser Arg Gly Ser Ile Met Ile
1               5                   10
```

IMMUNOLOGICALLY ACTIVE PROTEINS FROM *BORRELIA BURGDORFERI*

CROSS-REFERENCE TO RELATED APPLICATIONS

This application is a division of U.S. patent application Ser. No. 08/209,603, filed on Mar. 10, 1994, now U.S. Pat. No. 6,248,538, which in turn is a continuation of U.S. patent application Ser. No. 07/862,535, filed on Jun. 19, 1992, now abandoned, both of which are incorporated herein by reference. U.S. patent application Ser. No. 07/862,535 is a 371 filing of International Patent Application No. PCT/EP90/02282, filed on Dec. 21, 1990, which in turn is an international filing of German Patent Application No. P39 42 728.5, filed on Dec. 22, 1989, and of German Patent Application No. P40 18 988.0, filed on Jun. 13, 1990.

Lyme borreliosis is the commonest infectious disease of humans transmitted by ticks in the Federal Republic of Germany. In contrast to Russian spring-summer encephalitis (RSSE) which is likewise transmitted by ticks, Lyme borreliosis is not confined to a few endemic areas but occurs in all the states of the FRG. Infestation of the main vector in Europe, Ixodes ricinus, with the pathogen of Lyme borreliosis, the spirochete *Borrelia burgdorferi*, in Southern Germany is about 20% of adults, about 10% of nymphs and about 1% of larvae. The main vector in the USA, Ixodes dammini, may be up to 100% infected by Borrelia in highly endemic areas.

*B. burgdorferi* belongs to the family of spirochetes. Spirochetes are spiral bacteria 8–30 $\mu$m long. They consist of an outer coat, the endoflagella in the periplasm and the protoplasmic cylinder. The protoplasmic cylinder is a complex of cytoplasm, internal cell membrane and peptidoglycan. Representatives of the spirochetes which are pathogenic for humans include, beside *B. burgdorferi*, the Borrelia of relapsing fever (for example *B. recurrentis*), the pathogen of syphilis (*Treponema (T.) pallidum*) and the Leptospira. As a result of the close immunological relationship of the pathogens, cross-reactions are a problem in the serological detection of antibodies in cases of syphilis and Lyme borreliosis with assays currently available.

Infection with *B. burgdorferi* results in a complex clinical picture which can, similarly to syphilis, be divided into three different stages. The principal manifestations are:

| Early phase: | Stage I | Erythema migrans |
| | | Bannwarth's lymphocytic |
| | | meningoradiculitis (LMR) |
| | | Borrelia lymphocytoma |
| Late phase: | Stage III | Lyme arthritis |
| | | Acrodermatitis chronica |
| | | atrophicans (ACA) |
| | | Chronic Borrelia |
| | | encephalomyelitis |

Less common clinical manifestations are: carditis, myositis, iritis and panophthalmitis. Transmission by the pathogen crossing the placenta is possible but to date only a few cases of congenital Lyme borreliosis have been recorded. The various stages may occur singly or in combination. *B. burgdorferi* infection may also have a sdbclinical course. Epidemiological studies on 375 clinically confirmed cases show some peculiarities in the age and sex distribution of the various clinical manifestations. Thus, patients with Erythema migrans were commonest in the 30 to 60 year age group. Neurological manifestations showed two peaks with age: the first in children and young people up to 20 years of age, and the second in 40 to 70 year-olds. Lyme arthritis was observed to be commonest in 30 to 60 year-olds. Patients with ACA were never below 30 years of age. ACA affects women distinctly more often than men. Serological testing showed predominantly positive IgM findings in patients with Erythema migrans, and predominantly positive IgG findings when there were neurological manifestations, in an immunofluorescence assay. With the late manifestations of ACA and Lyme arthritis, the IgG titers were regularly elevated, and IgM antibodies were now detectable only in exceptional cases.

Available for diagnosis are both pathogen detection and antibody detection. Pathogen detection in material from patients (skin biopsies, CSF, puncture fluids) is recommended especially in the early stage (Erythema migrans) when antibody detection is frequently negative. However, a complex nutrient medium is required for culturing *B. burgdorferi* (Preac-Mursic, V.; Wilske, B.; Schierz, G. (1986): European *Borreliae burgdorferi* isolated from humans and ticks—culture conditions and antibiotic susceptibility. Zbl. Bakt. Hyg. A 163, 112–118) and cultivation is therefore restricted to special laboratories. In addition, a time of up to 5 weeks is required to isolate the pathogen. *B. burgdorferi* is isolated from skin samples in 50–70% of cases with cutaneous manifestations and in 3–5% of cases with neuroborreliosis (Preac-Mursic, V.; unpublished results).

Antibody detection (IgM, IgG) is carried out on serum and, when there are neurological manifestations, also from CSF. The serological finding depends on the stage of the disease, the duration of the symptoms and any antibiotic therapy which has already been applied. Thus, antibody detection with assays available to date is successful only in 20–50% of cases with Erythema migrans, in 50–90% of cases with neurological manifestations and in 90–100% in cases with ACA and arthritis.

Therapy of Lyme borreliosis is predominantly carried out with penicillin G, tetracyclines, erythromycin or cephalosporins. Although Lyme borreliosis frequently resolves spontaneously in the early stages, even then late manifestations are not ruled out. This is why therapy in the early stage is indispensable. In addition, clinical resolution after antibiotic therapy can be achieved when there are late manifestations only in some of the cases (for example only about 50% of cases with Lyme arthritis).

This is why Lyme borreliosis should be diagnosed as early as possible. Since (as already explained) pathogen isolation is costly, time-consuming and, moreover, not always successful, better serodiagnostic assays ought to be developed. The methods used to date (immunofluorescence assay (IFA), indirect hemagglutination assay (IHA), enzyme-linked immunosorbent assay (ELISA)) frequently fail in the early stages. The antigens employed for these assays are all *B. burgdorferi* cells or whole-cell ultrasonicates. The use of different *B. burgdorferi* strains as antigen in the ultrasonicate ELISA leads to differing test results. Immobilization of cells on slides or ultrasonicate antigen on microtiter plates is followed by incubation with serum or CSF and detection of the Borrelia-specific antibodies with a second fluorescence- or peroxidase-labeled antibody of the appropriate immunoglobulin class. The reaction is then quantified either in a fluorescence microscope (IFA) or after a color reaction in a photometer (ELISA).

Broad cross-reactions of the pathogen *B. burgdorferi* with other bacterial pathogens, especially with *T. pallidum*, the syphilis pathogen, is a problem for the specificity of the assays. Since the assay antigens generally consist of lysates of the whole pathogen there is also detection of antibodies against so-called common antigens (Hansen, K.; Hindersson, P.; Pedersen, N. S. (1988): Measurement of antibodies to the Borrelia burgdorferi flagellum improves serodiagnosis in Lyme disease. J. Clin. Microbiol., 26, 338–346). common antigens are widely distributed proteins with highly conserved sequences, that is to say the common antigens of Borrelia, Treponema as well as many other bacteria have common epitopes. Besides this, false-positive reactions may occur in the IgM-IFA or IgM-ELISA when the sera have rheumatoid factor activity. Therefore, in order to make the assays more specific, in the detection of IgG and IgM antibodies a preabsorption of the sera with a Treponema ultrasonicate, and additionally for the detection of IgM antibodies also absorption with rheumatoid factor absorbent, is carried out.

An object of the present invention is therefore to provide immunologically active proteins from Borrelia burgdorferi which are used in an assay kit which does not have the abovementioned disadvantages. An additional aim is that this assay kit makes it possible rapidly and reliably to detect antibodies directed against Borrelia burgdorferi.

Another object of the present invention is to provide monoclonal antibodies which are directed against particular immunologically active proteins from Borrelia burgdorferi. A further aim is to provide immunologically active proteins which are suitable as vaccines against infections caused by Borrelia strains.

Testing of patients' sera from different stages of the disease of Lyme borreliosis in a Western blot, and testing of non-Lyme borreliosis patients (especially syphilis patients) for cross-reactivity with B. burgdorferi resulted in the finding of immunologically active proteins (B. burgdorferi antigens) which, on the one hand, elicit a good antibody response after infection and, on the other hand, show a low cross-reactivity with sera which are not B. burgdorferi-positive (Example 1). It emerged that a particular strain of B. burgdorferi which has the internal laboratory identifier PKo and which was deposited at the Deutsch Sammlung für Mikroorganismen (DSM) under No. 5662 possesses, inter alia, an immunodominant protein in the molecular-weight region about 22 kD (pC protein). Under the provisions of the Budapest Treaty, representative samples of the Borrelia burgdorferi strain (internal laboratory identifier PKo) were deposited at the DSM Deutsche Sammlung von Mikroorganismen und Zelikulturen GmbH, Mascheroder Weg 1 B, D-3300 Braunschweig, Germany, under accession number DSM 5662, on Nov. 30, 1989. The molecular weight of the proteins according to the invention was determined by methods known per se, in particular by SDS gel electrophoresis. It was found that this protein is immunodominant for the IgM response. This protein is not expressed in the same way in all B. burgdorferi strains. This immunologically active protein (pC protein) was prepared by genetic manipulation according to the invention (Example 3).

Other immunologically active proteins (antigens) which are particularly suitable for use in assay kits were also prepared in generally accessible and commercially available Escherichia coli cells such as, for example, strains JM 105 (Pharmacia) or DH 5 (Gibco-BRL). To do this, the B. burgdorferi DNA fragments coding for these proteins were isolated and subsequently inserted into efficient expression vectors (Examples 2 and 3).

The appropriate DNA fragments were identified and isolated by various methods. Thus, an immunologically active protein with a molecular weight of about 41 kD, which is also called p41 protein hereinafter, was prepared by means of the polymerase chain reaction (PCR) and specific primers whose sequences were prepared by synthesis (Example 2).

In addition, a gene bank of the B. burgdorferi genome was constructed and was screened using monoclonal antibodies for the direct expression of immunologically active proteins.

In a corresponding way, proteins with molecular weights of about 100 kD and 31 kD were also cloned and sequenced.

Another method comprised purifying particular selected immunologically active proteins (antigens) from B. burgdorferi lysates and determining the amino-acid sequences of these antigens. Subsequently, oligodeoxynucleotides corresponding to the amino-acid sequence were synthesized and, by hybridization, those clones in the gene bank which have DNA sequences coding for the immunologically active proteins were identified. The two latter methods are explained in detail in Example 3.

After characterization, sequencing and recloning of the genes into appropriate expression vectors, the antigens were expressed in E. coli cells and subsequently purified. A preferred purification method is described in Example 4.

The immunologically active proteins from Borrelia burgdorferi which have been prepared according to the invention can be used in assay kits which provide a surprisingly sensitive detection of antibodies against B. burgdorferi in various test fluids. One advantage of the immunologically active proteins prepared according to the invention is that the preparations consist only of the required protein and possibly those proteins which are attributable to degradation events and/or incomplete translation. These preparations contain no B. burgdorferi proteins which do not correspond to the protein produced by recombination because they have been prepared by genetic manipulation.

The term "assay kits" means a set of assay reagents which makes it possible to detect particular antibodies. The principles on which assay kits are based have been described in "Immunoassays for the 80s" (1981) by A. Voller et al., published by MTP Press Ltd., Falcon House, Lancaster, England. The assay reagents display as principal component the antigen(s) and, where appropriate, specific, preferably monoclonal, antibodies.

The assay kits according to the invention for detecting antibodies against Borrelia burgdorferi contain at least one immunologically active protein which is available without contamination by other proteins from the Borrelia burgdorferi strain. This immunologically active protein acts as antigen and reacts with the antibodies present in the test fluid. Assay kits according to the invention preferably have two to four immunologically active proteins which are available without contamination by other proteins from B. burgdorferi. The assay kit furthermore contains an indicator component which makes the detection of the presence of complexes of antigen and antibody possible.

The assay kits according to the invention can be based on a variety of principles known per se. In principle, the antigen can carry a label, and the label can consist of a radioactive isotope or an enzyme which catalyzes a color reaction. It is likewise possible for the antigen to be bound to a solid support (microtiter plates or beads), and the indicator component can comprise an antibody which is directed against antibodies and carries a label, and the label can comprise a radioactive isotope or an enzyme which catalyzes a color reaction.

The assay kit preferred for the purposes of the present invention is the so-called ELISA (enzyme-linked immunosorbent assay). One embodiment thereof is described in detail in Example 5. The results of this example show that it was surprisingly possible to achieve a very high specificity of the assay kit by using only one immunologically active protein according to the invention. Furthermore, the assay kits according to the invention surprisingly make possible a differentiation correlated with the stage of the disease. The combined use of a plurality of antigens in one assay kit makes it possible to detect antibodies against Borrelia burgdorferi even in cases in which the symptoms of the disease have not yet become clinically manifest. It is likewise possible to diagnose infections with B. burgdorferi in which the patient experiences only a subclinical infection. The information which can be obtained from the assay kits according to the invention is particularly important in cases in which it has been possible to find a tick bite but it is unclear whether an infection with a Borrelia strain is present.

Combined use of a plurality of the immunologically active proteins is preferred for the purpose of the present invention. A combination of the proteins p41, pC, p17 and/or p100 is very particularly preferred. The use of the ELISA assay kit preferred according to the invention also makes possible a differentiation with regard to the nature of the antibodies. If, for example, IgM antibodies are to be detected, the so-called μ capture assay can be employed, in which antibodies directed against IgM antibodies are bound to the solid phase. After the assay plates have been incubated with the fluid to be tested, the IgM antibodies present in the test fluid are bound to the solid phase. It is then possible, after saturation of non-specific bindings, to add an immunologically active protein of the present invention. This antigen is then detected by an indicator molecule. In this case the antigen can be biotinylated, and subsequently avidin which has covalently bonded peroxidase is added. The peroxidase then catalyzes a reaction which leads to color formation.

Another possibility comprises adding monoclonal antibodies, which are specific for the antigen and are biotinylated, to the complex of support/anti-IgM antibody/antibody to be detected/antigen according to the invention. Biotinylation is described, for example, in Monoklonale Antikorper [Monoclonal antibodies] (1985) Springer Verlag, J. H. Peters et al. Detection of the complex is effected therein by adding avidin to which an enzyme catalyzing a color reaction is coupled.

Another embodiment of the present invention comprises detecting IgM by indirect ELISA. This entails the antigens according to the invention being bound to microtiter plates, incubated with the fluid to be detected and, after washing, the immune complexes being detected by means of anti-μ conjugate.

Another aspect of the present invention comprises a generation of monoclonal antibodies which are directed against the immunologically active proteins of Borrelia burgdorferi. The preparation of monoclonal antibodies of this type is explained in detail in Example 6. It is possible to use monoclonal antibodies of this type as reagents for direct pathogen detection. However, monoclonal antibodies can also be coupled to the solid phase of a microtiter plate. The immunologically active proteins (antigens) are added and then immobilized by antibody-antigen binding to the microtiter plate. The test fluid (which can be, for example, serum or CSF) is subsequently added. The antibodies present in the test fluid then bind to the antigen and can be detected with the aid of an indicator component.

Furthermore, the monoclonal antibodies can be used very satisfactorily for purifying immunologically active proteins (antigens). The advantage in this case is that the purification is particularly gentle. To do this, the monoclonal antibodies are bound to a solid matrix. This solid matrix is preferably in the form of a column. The partially prepurified antigens are then mixed under physiological conditions with the antibodies coupled to a solid matrix. After the matrix-antibody-antigen complex has been washed it is possible to elute the antigens. It is normal to use for this high salt concentrations or buffers with a pH which makes the elution possible.

In another aspect of the present invention, DNA sequences which correspond in whole or in part to the amino-acid sequence of the immunologically active proteins are provided. These DNA sequences can preferably be used to detect Borrelia strains in test material by hybridization. To do this, an oligonucleotide which partly corresponds to the DNA sequence is prepared. This oligonucleotide is radioactively labeled. On the other hand, the DNA from the test material is bound to a suitable filter, preferably nitrocellulose, and subsequently hybridized with the radioactively labeled oglionucleotide. It is likewise possible to use the DNA sequences according to the invention for in situ hybridization for direct detection of B. burgdorferi in infected tissue. In place of the chemically synthesized oligonucleotides it is also possible for appropriate DNA fragments to be replicated in bacteria and subsequently cut out of the vectors with the aid of restriction endonucleases. After isolation of these DNA fragments they can be radioactively labeled and used as described above for the hybridization.

Another aspect of the present invention comprises the possibility of using the immunologically active proteins (antigens) according to the invention from Borrelia burgdorferi as vaccines. To do this, the antigens according to the invention are prepared in pure form. They are subsequently administered, singly of in combination with or without an agent stimulating the immune response, to the person to be immunized. This stimulates the formation of specific antibodies against Borrelia burgdorferi strains.

The proteins, DNA sequences and monoclonal antibodies according to the invention can be used in various areas. Thus, the assay kits according to the invention can also be used to detect B. burgdorferi infections in livestock, and the proteins can also be used for immunizing livestock, especially valuable livestock.

To the extent that the present invention relates to proteins from Borrelia burgdorferi, these can also be protein fragments which have only a partial sequence of the complete amino-acid sequence. Partial sequences of this type usually have at least 10 amino acids and preferably at least 15 amino acids.

However, the protein fragments are normally larger. Thus, for example, it has been found with the protein with a molecular weight of about 41 kD that deletion of about 20 to 25 amino acids at the N terminus of the protein leads to a protein which has an increased specificity. The reason for this might be that a so-called common epitope is deleted and specific epitopes remain. The use of proteins with deletions of this type is particularly preferred in this connection.

Proteins with a molecular weight of about 22 kD or 100 kD are particularly preferred for the purpose of the present invention. These proteins can also derive from other Borrelia burgdorferi strains.

The preferred embodiments of the present invention are explained in detail by means of the following tables, figures and examples.

EXAMPLE 1

Determination of the Immunorelevant and Genus-specific Borrelia Proteins

Specific, commonly occurring serum antibodies, which are directed against particular individual B. burgdorferi antigens, show minimum cross-reactivity with proteins of related pathogens and, in addition, permit correlation with the individual stages of the disease of Lyme borreliosis, were sought.

The Western blot was used to search for commonly recognized antigens. To do this, a bacterial extract of *B. burgdorferi* (PKo strain) (Preac-Mursic, V.; Wilske, B.; Schierz, G. (1986): European *Borreliae burgdorferi* isolated from humans and ticks—culture conditions and antibiotic susceptibility. Zbl. Bakt. Hyg. A 163, 112–118) was pelleted, resuspended in PBS/NaCl and treated with ultrasound and then fractionated by SDS polyacrylamide gel electrophoresis (Laemmli, U. K. (1970): Cleavage of structural proteins during the assembly of the head of bacteriophage T4. Nature 227, 680–685).

The gels consisted of a collecting gel with pockets for the samples and a separating gel. The separating gels had the following composition: 15% acrylamide (Bio-Rad), 0.026% diallyltartardiamide (DATD, Bio-Rad) per percent acrylamide, 0.15% SDS, 375 mM Tris-HCl pH 8.5, 0.14 mM ammonium peroxodisulfate (AMPER, Bio-Rad) and 0.035% N,N,N',N'-tetramethylethylenediamine (TEMED, Bio-Rad). AMPER and TEMED acted in this case as the radical initiators for the polymerization. 2–4 h after the polymerization, the collecting gel (3.1% acrylamide, 0.08% diallyltartardiamide, 0.1% SDS, 125 mM Tris-HCl pH 7.0, 3 mM AMPER and 0.05% TEMED) was poured over the separating gel and provided with a Teflon comb. The anode and cathode chamber were filled with identical buffer solution: 25 mM tris base, 192 mM glycine and 0.1% SDS, pH 8.5.

In each case 20 µl of sample in lysis buffer (3% sucrose, 2% SDS, 5% β-mercaptoethanol, 20 mM Tris-HCl pH 7.0, bromophenol blue; heated at 100° C. for 5 min) were loaded per pocket. The electrophoresis was carried out at room temperature overnight with a constant current of 6 mA for gels 20×15 cm in size. The gels were subsequently transferred to nitrocellulose (NC).

For the protein transfer, the gel with the nitrocellulose lying on it was placed between Whatman 3 MM filter paper, conductive foam 1 cm thick and two carbon plates which conducted the current via platinum electrodes. Filter paper, foam and nitrocellulose were thoroughly impregnated with blot buffer (192 mM glycine, 25 mM tris base, 20% methanol, pH 8.5).

Transfer took place at 2 mA/cm² for 2 h. Free binding sites on the nitrocellulose were saturated for 1 h at 37° C. with Cohen buffer (1 mg/ml Ficoll 400, 1 mg/ml polyvinylpyrrolidone, 16 mg/ml bovine serum albumin, 0.1% NP 40, 0.05% Bacto gelatin in sodium borate buffer pH 8.2); (Cohen G. H., Dietzschold, B., Ponce de Leon, M., Long, D., Golub, E., Varrichio, A., Pereira, L. and Eisenberg, R. J.: Localisation and synthesis of an antigenic determinant of Herpes simplex virus glyco-protein D that stimulates the production of neutralizing antibodies. J. Virol. 49 (1984) 4183–4187). The blot was incubated with the patients' sera (1:100 dilution in 154 mM NaCl and 10 mM Tris-HCl pH 7.5) at room temperature overnight and with shaking.

After the serum incubation, the blot was washed with TTBS (50 m Tris-HCl pH 7.5, 500 mM NaCl, 0.01% Tween 20) four times for 15 minutes each time. The blot was then incubated with peroxidase-coupled anti-human immunoglobulin (DAKO, Hamburg, 1:1000 dilution in 154 mM NaCl and 10 mM Tris-HCl, pH 7.5) at room temperature for 2 h. The blot was washed several times with TTBS and then stained with 0.5 mg/ml diaminobenzidine and 0.01% hydrogen peroxide in 50 mM Tris-HCl pH 7.5. The staining was subsequently stopped with 1 N sulfuric acid, the blot was washed with water until free of acid and was dried between filter paper.

A selection of the reaction patterns of various sera with the Western blot strips is shown in FIGS. 1, 2a and b.

The following proteins proved to be immunodominant: p17 (17 kDa), pC (22 kDa), p41 (41 kDa) and p100 (100 kDa with variation in size in different *B. burgdorferi* isolates). Apart from p41, the biological functions of these antigens are unknown; p41 is the flagellin protein (Barbour, A. G. S., Hayes, S. F., Heiland, R. A., Schrumpf, M. E. and Tessier, S. L.: A Borrelia genus-specific monoclonal antibody binds to a flagellar epitope. Infect. Immun. 52 (1986) 549–554).

These analyses, which were carried out with a relatively large number of patients' sera from the various stages of the disease, provided evidence that not all *B. burgdorferi* infections are always detected with a single antigen. It emerged, in particular in the case of sera with IgM antibodies (recent infection), that a protein (pC) in the 22 kD region is particularly often recognized besides the flagellin (p41). However, simultaneous occurrence of both antibodies was not inevitable. It was possible to find sera which had only antibodies against p41 or only antibodies against the pC protein (FIG. 1 and 2a, Western blots). Detection of intrathecally formed antibodies in the CSF is of great importance in neuroborreliosis. IgG Western blots on 12 CSF/serum pairs from patients with Bannwarth's lymphocytic meningoradiculitis showed in all cases a local intrathecal immune response to p41. In the late stage, besides IgG antibodies against the flagellin, particularly found were antibodies against proteins in the 100 kD region (p100) and in the 17 kD region (p17) which were undetectable or only rarely detectable in the early stages. Thus, antibody reactivities with the p17 and p100 proteins are good markers for the attainment of stage III (FIG. 2b, Western Blot).

Improved standardization of the assays can be achieved with the aid of these four antigens.

The proteins p42, pC and p17 additionally show only a slight cross-reactivity with other bacterial strains, and the protein p100 proved to be a genus-specific protein with *B. burgdorferi*-specific epitopes. Tab. 2 (reactivity of immune sera against various bacterial pathogens with proteins from *B. burgdorferi*) summarizes the cross-reactivity of sera against various related pathogens with *B. burgdorferi* antigens according to Western blot analysis. It emerged from attempts to purify the four proteins (p41, pC, p17, p100) from *B. burgdorferi* extracts that large amounts of starting material are required. It was particularly difficult to purify p100, which is under-represented in the complete extract. Since cultivation is elaborate and costly it was necessary to look for possible ways of preparing these antigens by genetic manipulation. Western blot analysis of patients' sera has shown that virtually complete identification of all positive sera is possible with a combination of p41, pC, p17 and p100 produced by genetic manipulation as antigen and, furthermore, there is a correlation with the stage of the disease.

EXAMPLE 2

Production of p41 (Flagellin) from *B. Burgdorferi* in *Escherichia coli* by Genetic Manipulation The p41 coding region was obtained from a complete *B. burgdorferi* (DSM No. 5662 P/Ko2/85) DNA preparation by means of DNA amplification by a polymerase chain reaction (PCR). The sequence obtained in this way was subsequently placed under the control of inducible promoters and, after transfection into *E. coli*, expression was induced (Maniatis, T.; Fritsch, E. F.; Sambrook, J. (1982) Molecular cloning. Cold Spring Harbor).

For this purpose, the *B. burgdorferi* cells were cultivated for 2 weeks at 37° C. in 2 l of modified Barbour-Stoenner-Kelly (BSK) medium (Preac-Mursic, V.,; Wilske, B.; Schierz, G. (1986): European *Borreliae burgdorferi* isolated from humans and ticks—culture conditions and antibiotic susceptibility. Zbl. Bakt. Hyg. A 163, 112–118), pelleted at 6000 rpm, washed in TEN buffer (10 mM Tris-HCl pH 7.6; 1 mM EDTA; 10 mM NaCl) and resuspended in 20 ml of lysozyme buffer (20% sucrose, 50 mM Tris-HCl pH 7.6, 50 mM EDTA, 5 mg/ml lysozyme). After incubation at 37° C. for 30 min, the protoplasts produced by the action of lysozyme on the cell wall were lyzed by adding 1 ml of 25% SDS (sodium dodecylsulfate). After a further 10 min, 4 ml of a 5 M NaCl solution were added. Protein was denatured by adding an equal volume of TE-saturated (TE: 10 mM Tris/HCl, pH 7.8, 1 mM EDTA) phenol. The phases were separated by centrifugation at 4° C. and 6500 rpm for 5 min. Using a pipette with a wide opening (to avoid shear forces) the upper DNA-containing aqueous phase was cautiously transferred into a fresh tube and subsequently extracted once again with the same volume of phenol/chloroform/isoamyl alcohol (1:1:0.04). After separation, the upper aqueous phase was again cautiously transferred into a new tube, and the DNA was precipitated with twice the volume of ethanol. After about 5 min, the DNA which has precipitated out in the form of long threads is removed by winding onto a glass rod and is transferred into a 70% ethanol solution for washing. The DNA bound by adhesion to the glass rod was subsequently stored at room temperature for 2 h in order to bring about evaporation of the ethanol, and was then transferred into 4 ml of TEN buffer. 1 $\mu$l portions of the complete *B. burgdorferi* DNA obtained in this way were amplified in 100 $\mu$l PCR mixtures.

The sequences chosen as specific primers for the polymerase-catalyzed amplification contained the information for the translational start and the 3' end of p41 (flagellin). The DNA sequences shown in FIG. 3 were used for this. The two oligodeoxynucleotides were synthesized in 1 $\mu$mol columns in a Milligen/Biosearch 8700 DNA synthesizer and, after cleavage with ammonia, roughly purified by ethanol precipitation and taken up in 400 $\mu$l of $H_2O$ in each case. 1 $\mu$l portions of this oligodeoxynucleotide solution were employed for each PCR mixture; the buffers, nucleotides and the Taq polymerase originated from a commercially obtainable assay kit (Cetus/Perkin-Elmer, Überlingen) and were also used in accordance with the assay descriptions.

The temperature conditions for the individual cycles were:

| | |
|---|---|
| 2 min denaturation at | 94° C. |
| 2 min annealing at | 45° C. |
| 4 min DNA synthesis at | 73° C. |

50 cycles were carried out.

The mixtures from the PCRs were subsequently combined, and the DNA was precipitated, after adding NaCl in a final concentration of 0.2 M, with 2.5 times the amount of ethanol at −20° C. for 5 h. After pelleting and washing in 70% ethanol, the DNA was dissolved in 200 $\mu$l of $H_2O$ and, after addition of appropriate buffers, cleaved with the restriction enzymes Bam HI and Pst I (Boehringer Mannheim) as stated by the manufacturer. Fractionation by gel electrophoresis in a 1.5% agarose gel was followed by isolation of the amplified DNA fragment (about 1000 bp) and insertion into a pUC8 vector (Pharmacia) cut with BamHI and PstI (Vieira, J.; Messing, J. (1982): The pUC plasmids, and M13mp7-derived system for insertion mutagenesis and sequencing with synthetic universal primers. Gene 19, 259–268), using 0.25 $\mu$g of the vector, 0.5 $\mu$g of the p41 fragment and 2U of T4 DNA ligase with buffer as specified by the manufacturer (Boehringer Mannheim).

The ligated DNA fragments were transformed into the *E. coli* strain JM 109 (Pharmacia) (Yanisch-Perron, C.; Vieira, J.; Messing, J. (1985): Improved M13 phage cloning vectors and host strains: nucleotide sequences of the M13mp18 and pUC19 vectors. Gene 33, 103–119) and plated out on agar plates containing ampicillin (50 $\mu$g/ml) and X-Gal (30 $\mu$g/ml), and then white colonies were cultured in 5 ml of L broth medium, and the isolated plasmids were investigated for their inserts by restriction enzyme cleavage.

The *B. burgdorferi* flagellin-encoding DNA fragment is thus located behind the inducible lacUV5 promoter of the vector in the same reading frame as the lacZα-encoding transcript started by this promoter. This results in a flagellin which contains a few pUC8-encoded amino acids at its N terminus. This region is detailed below:

```
ATG ACC ATG ATT ACG AAT TCC CGG GGA TCC ATC ATG ATT (SEQ ID NO:1)

MET THR MET ILE THR ASN SER ARG GLY SER ILE MET ILB (SEQ ID NO:16)
                                 pUC8              p41
```

Liquid cultures of positive *E. coli* clones (for example pUc8 ly13) which contained the vector with DNA insert of the expected length (1000 bp) were again set up, and transcription from the lac promoter of the plasmid was induced by induction with 1 mM IPTG shaken at 37° C. for 3 hours. 1.5 ml of these cultures were then briefly pelleted, the bacteria were lyzed with boiling mix (3% sucrose, 2% SDS, 5% β-mercaptoethanol, 20 mM Tris-HCl pH 7.0, 2% bromophenol blue) at 100° C. for 10 min, and the proteins were fractionated by means of 17.5% SDS-PAGE. Staining.of the proteins with Coomassie brilliant blue revealed a new additional band at about 41 kD, which corresponds to the expected size of flagellin, for the cells with plasmid insert. A specific reaction of this recombinant antigen with a serum from a Lyme borreliosis patient and with a monoclonal antibody against *B. burgdorferi* p41 flagellin is demonstrated by the immunoblot shown in FIG. 4.

Every other inducible plasmid which starts a transcript in the same reading frame is also suitable just like pUC8 for the production of p41. Expression of an authentic p41 which has no foreign amino acids fused on is possible by cleaving the p41-encoding region at the translation start with BspHI (TC ATG A) and PstI (at the 3' end) and inserting the fragment into the NcoI site (CC ATG G) and PstI site of a so-called ATG vector.

The clone pUC8ly17 was used for the methods indicated hereinafter.

EXAMPLE 3

Production of pC, OspA and p100 in *E. coli* from *B. burgdorferi* Gene Banks

To prepare *B. burgdorferi*-specific DNA sequences, a chromosomal gene bank was set up in *E. coli*. It was possible with the aid of suitable methods such as immunoscreening or hybridization with selected oligonucleotides to identify in this gene bank *E. coli* clones which contained corresponding *B. burgdorferi*-specific DNA sequences. A restriction enzyme map was constructed after restriction enzyme analysis. It was possible to use this to transfer the DNA sequences which were sought specifically into expression vectors and to carry out sequencing thereof. The specific procedures for this were as follows: to isolate *B. burgdorferi* (DSM No. 5662) DNA (chromosomal DNA and plasmid DNA), the cells were cultivated as described in Example 2. After centrifugation at 12,000 rpm for 20 minutes, the cells were washed and resuspended in SET buffer (20% sucrose, 50 mM Tris-HCl pH 7.6; 50 mM EDTA). The cell wall was partially cleaved by adding 15 mg/5 ml lysozyme for 20 minutes. The protoplasts from the cells were then lyzed by adding SDS (n-dodecyl-sulfate sodium salt) final concentration 1%. After 20 minutes at 37° C., proteinase K (final concentration 1 mg/ml) was added for 1 hour twice, and the DNA-containing solution was adjusted to 100 mM NaCl with TEN buffer (10 mM Tris-HCl pH 7.6, 1 mM EDTA, 300 mM NaCl). One phenol extraction and two further phenol/chloroform/iso-amyl alcohol extractions (phenol:chloroform in the ratio 1:1; chloroform:isoamyl alcohol in the ratio 24:1) were carried out. The supernatant extracted in this way was mixed with 2.5 vol. of 95% ethanol, and the DNA was precipitated at −20° C. It was possible to obtain the DNA by winding the precipitated threads onto a glass rod and to wash it in 70% ethanol. After brief drying in a desiccator, the DNA was taken up in TE buffer (10 mM Tris-HCl pH 7.6, 1 mM EDTA) which contained RNAse (20 μg/ml). The DNA prepared in this way was used for the subsequent steps.

*B. burgdorferi* DNA was incubated with the restriction enzyme Sau 3A (Boehringer, Mannheim) as stated by the manufacturer. Partial cleavage of the DNA was achieved by choosing suitable enzyme dilutions and the time the enzyme acted thereon. Partially cleaved DNA obtained in this way was ligated with vector DNA (pUC18 or other suitable vector DNA) which had been restricted with BamH I and dephosphorylated by treatment with alkaline phosphatase. T4 DNA ligase (Boehringer Mannheim) was employed as specified by the manufacturer for this. 0.2–0.5 μg/μl complete DNA was employed per transformation mixture. *E. coli* JM 109 (or other suitable *E. coli* strains) were transformed with the ligated DNA by the protocol of Hanahan (Hanahan, D. (1985): Techniques of Transformation of *Escherichia coli*, pp. 109–135. In: D. M. Glover (ed.) DNA cloning, Vol. 1. A practical approach. IRL Press, Oxford) or as described by Maniatis et al. (Maniatis, T. (1982): Molecular cloning: a laboratory manual. Cold Spring Harbor Laboratory, Cold Spring Harbor, N.Y.). Recombinant *E. coli* clones were selected and cultivated on LB medium (10 g of tryptone, Difco, 5 g of yeast extract, Difco, 5 g of NaCl, Merck) which contained 100 μg/ml ampicillin (or another suitable antibiotic). The colony pattern was transferred identically to LB plates, and colony replicas on nitrocellulose were produced. The cells in these colony replicas were lyzed in different ways on the filter depending on the screening method used. When mono- or polyclonal sera (immunoscreening) were used to detect *B. burgdorferi*-specific gene products induced by the DNA inserted by recombination, the cells were lyzed over saturated chloroform vapor for 15 min. After saturation of the filter treated in this way with a skimmed milk solution for 2 hours, the filters were incubated with the various sera overnight, washed several times with TTBS buffer (see above) and incubated with the second peroxidase-conjugated antibody (Dako, Hamburg) for 2 hours. Renewed washing with TTBS buffer served to reduce non-specifically bound peroxidase-conjugated antibodies. It was possible to identify positive, that is to say *B. burgdorferi* antigen-producing *E. coli* clones by enzymatic conversion of the substrates diaminobenzidine (Sigma-Chemie, Munich) and $H_2O_2$ into an insoluble brown pigment. The positive *E. Coli* clones identified in this way were inoculated from the initial plate and analyzed. When specific oligonucleotides were used for the hybridization and thus for the detection of specific *B. burgdorferi* antigen sequences (screening by hybridization), the cells underwent alkaline lysis on the nitrocellulose filter (Schleicher & Schuell) (by wetting the filters with 0.5 M NaOH, 1.5 M NaCl for 5 minutes). After neutralization (by wetting the filters in 1.5 M NaCl, 0.5 M Tris-HCl pH 8.0 for 5 minutes), the filters with the denatured DNA were wetted with 2×SSPE (20×SSPE: 3.6 M NaCl, 200 mM $NaH_2PO_4$, pH 7.4, 20 mM EDTA, pH 7.4) and dried. The DNA was immobilized by baking the filters at 80° C. for 2 hours. The filters treated in this way were then employed for the hybridization. The hybridization was carried out using radioactive ($^{32}P$) and non-radioactive (for example digoxigenin, Boehringer Mannheim) as detection methods. The labeling methods for this were known (Maniatis, T. (1982): Molecular cloning: a laboratory manual. Cold Spring Harbor Laboratory, Cold Spring Harbor) or recommended by the manufacturer (Boehringer Mannheim) ($^{32}P$ labeling with $^{32}P$-gamma-ATP and kinase reaction or digoxigenin labeling with Dig-11-UTP and terminal transferase reaction). A restriction enzyme analysis was drawn up for positive *E. coli* clones and, with this information, expression of the antigen-encoding DNA sequences in suitable vectors, and sequencing thereof, were carried out.

The hybridization probes employed at the start were synthetic oligodeoxynucleotides whose sequence had been selected on the basis of p100 and pC amino-acid sequences.

The procedure for this was as follows:

The two proteins were partially purified from lysates of *B. burgdorferi* by extraction with n-octyl β-D-thioglucopyranoside and further fractionated by SDS-polyacrylamide gel electrophoresis. The antigens were subsequently transferred by Western blotting to a glass fiber matrix, and the appropriate pieces with the *B. burgdorferi* proteins were cut out. p100 then underwent partial N-terminal sequencing, and the first 22 amino acids of the amino terminus were determined (this method of microsequencing is described in: Eckerskorn, C., Mewes, W., Goretzki, H. and Lottspeich, F.: A new siliconized fiber as support for protein-chemical analysis of electroblotted proteins. Eur. J. Biochem. 176 (1988) 509–519). In the case of pC, direct partial sequencing was not possible since the N terminus is not directly amenable to sequencing, that is to say that it is possible that myristylation or similar modifications are present. For this reason, this protein was cleaved with trypsin, the fragments were fractionated by HPLC, and two of them were then partially sequenced. The oligodeoxynucleotide sequences specified hereinafter were then derived from the amino-acid sequences obtained in this way. Since in most cases there are several codon options for an amino acid, it was also necessary for the base variations and the appropriate sites on the oligonucleotide to be taken into account and incorporated during the synthesis in equimolar ratios.

p100-p1-p100-amino-acid sequence: (SEQ ID NO: 2)
  Glu Leu Asp Lys Glu Lys Leu Lys Asp Phe Val Asn Leu Asp Leu Glu Phe Val Asn Thr p-100-oligodeoxynucleotide sequence, (SEQ ID NO: 3) the bases indicated in parentheses and separated by ";" were incorporated during the synthesis (in a Milligen/Biosearch 8700 DNA synthesizer) in equimolar ratios:
  GA(G;A) (C;T)T(G;T;A) GA(C;T) AA(G;A) GA(G;A) AA(G;A) (C;T)T(G;T;A) AA(G;A) GA(C;T) TT(C;T) GT(T;A) AA(C;T) (C;T)T(G;T;A) GA(C;T) (C;T)A (G;T;A) GA(G;A) TT(C;T) GT(T;A) AA(C;T) TA(C;T) A The oligodeoxynucleotide sequence was used as probe and hybridized with the clones containing the B. burgdorferi DNA. Subcloning results in a clone which contains the gene for p100. The following coding DNA sequence of p100 (5' end) of the strain PKo was found for a length of 346 base pairs. (SEQ ID NO: 4)

5' ATG AAA AAA ATG TTA CTA ATC TTT AGT TTT
  TTT CTT GTT TTT TTA AAT GGA TTT CCT CTT
  AAT GCA AGG GAA GTT GAT AAG GAA AAA TTA
  AAG GAC TTT GTT AAT ATG GAT CTT GAA TTT
  GTT AAT TAC AAG GGT CCT TAT GAT TCT ACA
  AAT ACA TAT GAA CAA ATA GTA GGT ATT GGG
  GAG TTT TTA GCA AGG CCG TTG ATC AAT TCC
  AAT AGT AAG TCA AGT TAT TAT GGT AAA TAT
  TTT GTT AAT AGA TTT ATT GAC GAT CAA GAT
  AAA AAA GCA AGT GTT GAT ATT TTT TCT ATT
  GGT AGT AAG TCA GAG CTT GAT AGT ATA TTA
  AAT CTA AGA AGA ATT C . . . 3'

The following amino-acid sequence (SEQ ID NO: 5) was found after complete cloning:
  Met Lys Lys Met Leu Leu Ile Phe Ser Phe Phe Leu Val
  Phe Leu Asn Gly Phe Pro Leu Asn Ala Arg Glu Val Asp
  Lys Glu Lys Leu. Lys Asp Phe Val Asn Met Asp Leu
  Glu Phe Val Asn Tyr Lys Gly Pro Tyr Asp Ser Thr Asn
  Thr Tyr Glu Gln Ile Val Gly Ile Gly Glu Phe Leu Ala
  Arg Pro Leu Ile Asn Ser Asn Ser Asn Ser Ser Tyr Tyr
  Gly Lys Tyr Phe Val Asn Arg Phe Ile Asp Asp Gln Asp
  Lys Lys Ala Ser Val Asp Ile Phe Ser Ile Gly Ser Lys Ser
  Glu Leu Asp Ser Ile Leu Asn Leu Arg Arg Ile Leu Thr
  Gly Tyr Leu Ile Lys Ser Phe Asp Tyr Glu Arg Ser Ser
  Ala Glu Leu Ile Ala Lys Ala Ile Thr Ile Tyr Asn Ala Val
  Tyr Arg Gly Asp Leu Asp Tyr Tyr Lys Glu Phe Tyr Ile
  Glu Ala Ser Leu Lys Ser Leu Thr Lys Glu Asn Ala Gly
  Leu Ser Arg Val Tyr Ser Gln Trp Ala Gly Lys Thr Gln
  Ile Phe Ile Pro Leu Lys Lys Asn Ile Leu Ser Gly Asn Val
  Glu Ser Asp Ile Asp Ile Asp Ser Leu Val Thr Asp Lys
  Val Val Ala Ala Leu Leu Ser Glu Asn Glu Ser Gly Val
  Asn Phe Ala Arg Asp Ile Thr Asp Ile Gln Gly Glu Thr
  His Lys Ala Asp Gln Asp Lys Ile Asp Ile Glu Leu Asp
  Asn Phe His Glu Ser Asp Ser Asn Ile Thr Glu Thr Ile
  Glu Asn Leu Arg Asp Gln Leu Glu Lys Ala Thr Asp Glu
  Glu His Lys Lys Glu Ile Glu Ser Gln Val Asp Ala Lys
  Lys Lys Gln Lys Glu Glu Leu Asp Lys Lys Ala Ile Asp
  Leu Asp Lys Ala Gln Gln Lys Leu Asp Phe Ala Glu Asp
  Asn Leu Asp Ile Gln Arg Asp Thr Val Arg Glu Lys Leu
  Gln Glu Asn Ile Asn Glu Thr Asn Lys Glu Lys Asn Leu
  Pro Lys Pro Gly Asp Val Ser Ser Pro Lys Val Asp Lys
  Gln Leu Gln Ile Lys Glu Ser Leu Glu Asp Leu Gln Glu
  Gln Leu Lys Glu Ala Ser Asp Glu Asn Gln Lys Arg Glu
  Ile Glu Lys Gln Ile Glu Ile Lys Lys Asn Asp Glu Glu
  Leu Phe Lys Asn Lys Asp His Lys Ala Leu Asp Leu Lys
  Gln Glu Leu Asn Ser Lys Ala Ser Ser Lys Glu Lys Ile
  Glu Gly Glu Glu Glu Asp Lys Glu Leu Asp Ser Lys Lys
  Asn Leu Glu Pro Val Ser Glu Ala Asp Lys Val Asp Lys
  Ile Ser Lys Ser Asn Asn Asn Glu Val Ser Lys Leu Ser
  Pro Leu Asp Glu Pro Ser Tyr Ser Asp Ile Asp Ser Lys
  Glu Gly Val Asp Asn Lys Ser Val Asp Leu Gln Lys Thr
  Lys Pro Gln Val Glu Ser Gln Pro Thr Ser Leu Asn Glu
  Asp Leu Ile Asp Val Ser Ile Asp Ser Ser Asn Pro Val
  Phe Leu Glu Val Ile Asp Pro Ile Thr Asn Leu Gly Thr
  Leu Gln Leu Ile Asp Leu Asn Thr Gly Val Arg Leu Lys
  Glu Ser Ala Gln Gln Gly Ile Gln Arg Tyr Gly Ile Tyr
  Glu Arg Glu Lys Asp Leu Val Val Ile Lys Ile Asp Ser
  Gly Lys Ala Lys Leu Gln Ile Leu Asp Lys Leu Glu Asn
  Leu Lys Val Ile Ser Glu Ser Asn Phe Glu Ile Asn Lys
  Asn Ser Ser Leu Tyr Val Asp Ser Arg Met Ile Leu Val
  Val Val Lys Asp Asp Ser Asn Ala Trp Arg Leu Ala Lys
  Phe Ser Pro Lys Asn Leu Asp Glu Phe Ile Leu Ser Glu
  Asn Lys Ile Leu Pro Phe Thr Ser Phe Ala Val Arg Lys
  Asn Phe Ile Tyr Leu Gln Asp Glu Leu Lys Ser Leu Val
  Thr Leu Asp Val Asn Thr Leu Lys Lys Val Lys Amino-acid sequence of the p100 protein In an analogous manner, using pC amino-acid sequences:
  p1: (SEQ ID NO: 6) Lys Ile Thr Asp Ser Asn Ala Thr Val Leu Ala Val Lys
  p2: (SEQ ID NO: 7) Asp Leu Phe Glu Ser Val Glu Gly Leu Leu Lys the corresponding oligodeoxynucleotide sequences were synthesized:

pC-p1 oligodeoxynucleotide sequence: (SEQ ID NO: 8)
  AA(G;A) AT(T;A) AC(A;T) GA(T;C) (A;T)C(A;T) AA(T;C) GC(A;T) AC(A;T) GT(A;T) (T;C)T(G;A;T) GC(A;T) GT(A;T) AA(A;G) A pC-p2 oligodeoxynucleotide sequence: (SEQ ID NO: 9)
  GA(T;C) (C;T)T(G;A;T) TT(T;C) GA(G;A) (T;A)C(A;T) GT(A;T) GA(G;A) GG(A;T;C) (T;C)T(G;A;T) (T;C)T (G;A;T) AA(A;G) A After suitable clones have been found by hybridization and subcloning of the required gene it was possible to determine the following coding DNA sequence of pC of the strain PKo for a length of 639 base pairs: (SEQ ID NO: 10)

5' ATG AAA AAG AAT ACA TTA AGT GCG ATA TTA
  ATG ACT TTA TTT TTA TTT ATA TCT TGT AAT
  AAT TCA GGG AAG GTG GGG ATT CTG CAT CTA
  CTA ATC CTG CTG ACG AGT CTT GCG AAA GGG
  CCT AAT CTT ACA GAX ATA AGC AAA AAA ATT
  ACA GAT TCT AAT GCA TTT GTA CTT GCT GTT
  AAA GAA GTT GAG ACT TTG GTT TTA TCT ATA
  GAT GAA CTT GCT AAG AAA GCT ATT GGT CAA
  AAA ATA GAC AAT AAT AAT GGT TTA GCT GCT
  TTA AAT AAT CAG AAT GGA TCG TTG TTA GCA

GGA GCC TAT GCA ATA TCA ACC CTA ATA ACA
GAA AAA TTG AGT AAA TTG AAA AAT TTA GAA
GAA TTA AAG ACA GAA ATT GCA AAG GCT AAG
AAA TGT TCC GAA GAA TTT ACT AAT AAA CTA
AAA AGT GGT CAT GCA GAT CTT GGC AAA CAG
GAT GCT ACC GAT GAT CAT GCA AAA GCA GCT
ATT TTA AAA ACA CAT GCA ACT ACC GAT AAA
GGT GCT AAA GAA TTT AAA GAT TTA TTT GAA
TCA GTA GAA GGT TTG TTA AAA GCA GCT CAA
GTA GCA CTA ACT AAT TCA GTT AAA GAA CTT
ACA AGT CCT GTT GTA GCA GAA AGT CCA AAA
AAA CCT TAA 3'

The protein pC has the following sequences for a length of 212 amino acids: (SEQ ID NO: 11)

Met Lys Lys Asn Thr Leu Thr Ala Ile Leu Met Thr Leu
Phe Leu Phe Ile Ser Cys Asn Asn Ser Gly Lys Val Gly
Ile Leu Thr Ser Thr Asn Pro Ala Asp Glu Ser Ala Lys
Gly Pro Asn Leu Thr Glu Ile Ser Lys Lys Ile Thr Asp
Ser Asn Ala Phe Val Leu Ala Val Lys Glu Val Glu Thr
Leu Val Leu Ser Ile Asp Glu Leu Ala Lys Lys Ala Ile
Gly Gln Lys Ile Asp Asn Asn Asn Gly Leu Ala Ala Leu
Asn Asn Gln Asn Gly Ser Leu Leu Ala Gly Ala Tyr Ala
Ile Ser Thr Leu Ile Thr Glu Lys Leu Ser Lys Leu Lys
Asn Leu Glu Glu Leu Lys Thr Glu Ile Ala Lys Ala Lys
Lys Cys Ser Glu Glu Phe Thr Asn Lys Leu Lys Ser Gly
His Ala Asp Leu Gly Lys Gln Asp Ala Thr Asp Asp His
Ala Lys Ala Ala Ile Leu Lys Thr His Ala Thr Thr Asp
Lys Gly Ala Lys Glu Phe Lys Asp Leu Phe Glu Ser Val
Glu Gly Leu Leu Lys Ala Ala Gln Val Ala Leu Thr Asn
Ser Val Lys Glu Leu Thr Ser Pro Val Val Ala Glu Ser
Pro Lys Lys Pro

Amino-acid Sequence of the pC Protein—22 kD

In a corresponding way, a part of the coding DNA sequence of OspA (5' end) of the strain PKo was also determined for a length of 680 base pairs: (SEQ ID NO: 12)

5' ATG AAA AAA TAT TTA TTG GGA ATA GGT CTA
ATA TTA GCC TTA ATA GCA TGC AAG CAA AAT
GTT AGC AGC CTT GAT GAA AAA AAC AGC GCT
TCA GTA GAT TTG CCT GGT GAG ATG AAA GTT
CTT GTA AGT AAA GAA AAA GAC AAA GAC
GGT AAG TAC AGT CTA AAG GCA ACA GTA GAC
AAG ATT GAG CTA AAA GGA ACT TCT GAT AAA
GAC AAT GGT TCT GGG GTG CTT GAA GGT ACA
AAA GAT GAC AAA AGT AAA GCA AAA TTA ACA
ATT GCT GAC GAT CTA AGT AAA ACC ACA TTC
GAA CTT TTC AAA GAA GAT GGC AAA ACA TTA
GTG TCA AGA AAA GTA AGT TCT AAA GAC AAA
ACA TCA ACA GAT GAA ATG TTC AAT GAA AAA
GGT GAA TTG TCT GCA AAA ACC ATG ACA AGA
GAA AAT GGA ACC AAA CTT GAA TAT ACA GAA
ATG AAA AGC GAT GGA ACC GGA AAA GCT
AAA GAA GTT TTA AAA AAC TTT ACT CTT GAA
GGA AAA GTA GCT AAT GAT AAA GTA ACA TTG
GAA GTA AAA GAA GGA ACC GTT ACT TTA AGT
AAG GAA ATT GCA AAA TCT GGA GAA GTA ACA
GTT GCT CTT AAT GAC ACT AAC ACT ACT CAG
GCT ACT AAA AAA ACT GGC GCA TGG GAT TCA
AAA ACT TCT ACT TTA ACA ATT AGT GT . . . 3'

After complete sequencing it was possible to determine the following amino-acid sequence for the 31 kD protein: (SEQ ID NO: 13)

Met Lys Lys Tyr Leu Leu Gly Ile Gly Leu Ile Leu Ala Leu
Ile Ala Cys Lys Gln Asn Val Ser Ser Leu Asp Glu Lys
Asn Ser Ala Ser Val Asp Leu Pro Gly Glu Met Lys Val
Leu Val Ser Lys Glu Lys Asp Lys Asp Gly Lys Tyr Ser
Leu Lys Ala Thr Val Asp Lys Ile Glu Leu Lys Gly Thr
Ser Asp Lys Asp Asn Gly Ser Gly Val Leu Glu Gly Thr
Lys Asp Asp Lys Ser Lys Ala Lys Leu Thr Ile Ala Asp
Asp Leu Ser Lys Thr Thr Phe Glu Leu Phe Lys Glu Asp
Gly Lys Thr Leu Val Ser Arg Lys Val Ser Ser Lys Asp
Lys Thr Ser Thr Asp Glu Met Phe Asn Glu Lys Gly Glu
Leu Ser Ala Lys Thr Met Thr Arg Glu Asn Gly Thr Lys
Leu Glu Tyr Thr Glu Met Lys Ser Asp Gly Thr Gly Lys
Ala Lys Glu Val Leu Lys Asn Phe Thr Leu Glu Gly Lys
Val Ala Asn Asp Lys Val Thr Leu Glu Val Lys Glu Gly
Thr Val Thr Leu Ser Lys Glu Ile Ala Lys Ser Gly Glu
Val Thr Val Ala Leu Asn Asp Thr Asn Thr Thr Gln Ala
Thr Lys Lys Thr Gly Ala Trp Asp Ser Lys Thr Ser Thr
Leu Thr Ile Ser Val Asn Ser Lys Lys Thr Thr Gln Leu
Val Phe Thr Lys Gln Asp Thr Ile Thr Val Gln Lys Tyr
Asp Ser Ala Gly Thr Asn Leu Glu Gly Thr Ala Val Glu
Ile Lys Thr Leu Asp Glu Leu Lys Asn Ala Leu Lys

Amino-acid Sequence of OspA (Strain PKo)

EXAMPLE 4

Purification of the *B. burgdorferi* Antigens Produced by Recombination a) p41 (Flagellin) as Example A 50 ml overnight culture of the clone pUC8ly2 described in Example 2 was added to 1.5 ml of fresh L broth medium and incubated, shaking vigorously, at 37° C. When an optical density of 0.7 was reached, the culture was induced with IPTG in a final concentration of 1 mM and incubated for a further 3 h. The bacteria were pelleted (6000 rpm, 10 min), resuspended in 300 ml of 20 mM Tris-HCl pH 8.0, 50 mM EDTA, 0.5 mg/ml lysozyme and placed in a water bath at 37° C. for 45 min. Addition of NaCl in a final concentration of 150 mM and Triton-X-100 in a final concentration of 1% was followed by further incubation at 37° C. for 45 min, and the suspension was subsequently treated with ultrasound three times for 5 min each time. Insoluble constituents were pelleted at 9000 rpm for 30 min, resuspended in 20 mM Tris-HCl pH 8.0, 10 mM dithiothreitol and 1% octyl glucopyranoside (Sigma-Chemie, Munich) and stirred at room temperature for 1 h. After subsequent pelleting of insoluble constituents at 17,000 rpm for 30 min, the supernatant was cautiously decanted off.

The pellet was subsequently resuspended in 150 ml of 20 mM Tris-HCl pH 8.0, 8 M urea and 1% βmercaptoethanol by stirring for 2 h. Insoluble constituents were once again in this case removed by centrifugation at 17,000 rpm for 30 min, and the supernatant was pumped onto a DEAE Sephacel column (Pharmacia, Freiburg) with a gel volume of 550 ml (diameter 3 cm, height 80 cm). The p41 antigen was eluted in an NaCl gradient from 0 to 800 mM in a total volume of 600 ml. The recombinant p41 is eluted at an NaCl concentration of about 0.25 M.

The appropriate fractions were combined and further purified by HPLC with a Mono Q column (anion exchanger) (FIG. 4). An elution profile with the purified p41 in an NaCl gradient from 0 to 800 mM is shown in FIG. 5.

The fractions which were positive for p41 here (according to Western blot analysis) were dialyzed against 20 mM Tris-HCl pH 8.0, 10 mM $MgCl_2$ and 0.1% β-mercaptoethanol, and subsequently used for the assays shown in Example 5. The yield typically to be expected from purification of p41 starting from 1 l of bacterial culture is 5 to 10 mg.

It was possible to determine the following amino-acid sequence after sequencing: (SEQ ID NO: 14)

Met Arg Gly Ser Ile Met Ile Ile Asn His Asn Thr Ser Ala
Ile Asn Ala Ser Arg Asn Asn Ala Ile Asn Ala Ala Asn

Leu Ser Lys Thr Gln Glu Lys Leu Ser Ser Asn Tyr Arg
Ile Asn Arg Ala Ser Asp Asp Ala Ala Gly Met Gly Val
Ser Gly Lys Ile Asn Ala Gln Ile Arg Gly Leu Ser Gln
Ala Ser Arg Asn Thr Ser Lys Ala Ile Asn Phe Ile Gln
Thr Thr Glu Gly Asn Leu Asn Glu Val Glu Lys Val Leu
Val Arg Met Lys Glu Leu Ala Val Gln Ser Gly Asn Gly
Thr Tyr Ser Asp Ser Asp Arg Gly Ser Ile Gln Ile Glu Ile
Glu Gln Leu Thr Asp Glu Ile Asn Arg Ile Ala Asp Gln
Ala Gln Tyr Asn Gln Met His Met Leu Ser Asn Lys Ser
Ala Ser Gln Asn Val Lys Thr Ala Glu Glu Leu Gly Met
Gln Pro Ala Lys Ile Asn Thr Pro Ala Ser Leu Ser Gly
Ser Gln Ala Ser Trp Thr Leu Arg Val His Val Gly Ala
Asn Gln Asp Glu Ala Ile Ala Val Asn Ile Tyr Ser Ala
Asn Val Ala Asn Leu Phe Ala Gly Glu Gly Ala Gln Ala
Ala Gln Ala Ala Pro Val Gln Glu Gly Ala Gln Glu Glu
Gly Ala Gln iln Pro Thr Pro Ala Thr Ala Pro Thr Gln
Gly Gly Val Asn Ser Pro Val Asn Val Thr Thr Thr Val
Asp Ala Asn Thr Ser Leu Ala Lys Ile Glu Asn Ala Ile
Arg Met Ile Ser Asp Gln Arg Ala Asn Leu Gly Ala Phe
Gln Asn Arg Leu Glu Ser Ile Lys Asn Ser Thr Glu Tyr
Ala Ile Glu Asn Leu Lys Ala Ser Tyr Ala Gln Ile Lys
Asp Ala Thr Met Thr Asp Glu Val Val Ala Ala Thr Thr
Asn Ser Ile Leu Thr Gln Ser Ala Met Ala Met Ile Ala
Gln Ala Asn Gln Val Pro Gln Tyr Val Leu Ser Leu Leu Arg Amino-acid Sequence of the p41 Protein b) Purification of Recombinant *Borrelia burgdorferi* pC Antigen from *E. coli*

A clone which contains the gene for the PC antigen (pDS1PC5) is inoculated in 100 ml of L broth (containing 50 μg of ampicillin/ml), left to grow over-night and then transferred into 900 ml of L broth/ampicillin—2× concentrated yeast extract/2 ml of glycerol—and, after about 1 h, induced with 2 mM IPTG and shaken for a further 2–3 h.

The pellet, after centrifugation at 8000 rpm for 10 min, is resuspended in 20 ml of lysis buffer (50 mM Tris-HCl, pH 7.5, 2 mM EDTA, 0.1 mM DTE, 0.1 mM PMSF; 0.4 mg/ml lysozyme). Stirring at room temperature for 30 min is followed by addition of Triton-X 100 (final concentration 0.1–0.2%). Also added are 10 μl of Benzonase (Merck). Stirring at room temperature is continued for a further 30 min. The suspension which is now clear is adjusted to 1 M NaCl with solid NaCl and stirred for a further 30 min-60 min (at 4° C.).

After centrifugation at 4° C. and 15,000 rpm for 30 min, the pC protein is quantitatively present in the supernatant. The pellet is discarded. The supernatant is dialyzed against 10 mM Tris-HCl, pH 8.0, changing the buffer several times. Centrifugation and/or filtration is followed by loading onto DEAE Sepharose (Pharmacia), the column being equilibrated with 10 mM Tris-HCl, pH 8.0. On elution with 0 M NaCl, the pC protein appears in the second peak of the flow-through. The first fractions can be discarded, and the remainder is collected and rechromatographed. The separating column is regenerated with 1 M NaCl and equilibrated in 10 mM Tris-HCl pH 8.0. The antigen obtained in this way can now be used in a suitable assay kit, for example an ELISA.

c) Purification of Recombinant *Borrelia burgdorferi* OspA Antigen from *E. coli*

A clone which contains the gene for the OspA antigen (pDS10spA) is inoculated in 100 ml of L broth (containing 50 μg of ampicillin/ml) and cultured over-night. The culture broth is transferred into 900 ml of L broth/ampicillin—2× concentrated yeast extract/2 ml glycerol—and, after about 1 h, induced with 2 mM IPTG and shaken for a further 2–3 h.

The cells are centrifuged at 6000 rpm for 5 min, and the pellet is resuspended in 20 ml of lysis buffer (50 mM Tris-HCl, pH 7.5, 2 mM EDTA, 0.1 mM DTE, 0.1 mM PMSF; 0.4 mg/ml lysozyme). Stirring at room temperature for 30 min is followed by addition of Triton-X 100 (final concentration 0.5–1%). Also added are 10 μl of Benzonase (MERCK). This is followed by stirring at room temperature for a further 30 min.

The suspension which is now clear is adjusted to 1 M NaCl with solid NaCl and stirred further (at 4° C.). After centrifugation at 4° C. and 15,000 rpm for 30 min, OspA is virtually quantitatively present in the pellet. The supernatant is discarded, and the pellet is resuspended in 2 M urea (with 50 mM Tris-HCl, pH 7.5, 2 mM EDTA, 0.1 mM DTE). OspA is now in the supernatant.

The supernatant is dialyzed in a dialysis tube against 5 mM MES (2-[N-morpholino]ethanesulfonic acid) buffer, pH 6.0, it being absolutely necessary to change the buffer several times. After centrifugation and filtration, the protein is loaded onto an *S Sepharose* fast-flow (Pharmacia) column. It is first washed with 0 M NaCl and then eluted with a gradient from 0 to 1 M NaCl. The OspA antigen elutes as a sharp peak at about 0.4 M NaCl. After dialysis against 10 mM Tris-HCl pH 7.5, the OspA antigen can be used in a suitable assay kit, for example an ELISA.

EXAMPLE 5

Use of *B. burgdorferi* Antigens Produced by Recombination (p41 as Example) in an ELISA Owing to the high purity of the recombinant antigens produced, it is possible to carry out *B. burgdorferi*-specific assays which are machine-readable and can be carried out without great technical and personnel expenditure.

Microtiter plates were coated with 50 μl of the purified p41 (concentration 0.5–5 μg/l) per well. The plates. were incubated by standard methods at 4° C. overnight, washed, and the binding sites which were still free were saturated with 2% strength bovine serum albumin solution. Subsequently, 50 μl of serum (dilution 1:200) were pipetted into each and incubated at 37° C. for 2 h, unbound portions were washed out and the bound immune complexes were detected with 50 μl of peroxidase-labeled anti-human IgG (dilution 1:1000) in each case. Another wash was followed by each of the wells being charged with 100 μl of ortho-phenylenediamine (concentration 0.1% in 0.1 M phosphate buffer pH 6.0 with 0.03% $H_2O_2$) as color reagent, and the staining was carried out in the dark and stopped with 100 μl of 1 N sulfuric acid after 10 min. The microtiter plate was evaluated in a photometer at 486 nm (FIG. 6).

In the example shown here, 7 positive and 8 negative anti-*B. burgdorferi* sera were tested. Three of the clinically confirmed Lyme-positive sera showed no reaction with p41 on Western blot strips with *B. burgdorferi* as antigen, that is to say were sera from the early stage of infection. These likewise showed only marginal reaction in an ELISA with the recombinant antigen. By contrast, normally p41-positive sera reacted very well, whereas Lyme-negative sera remained in the range below OD=0.3.

EXAMPLE 6

Preparation of *B. Burgdorferi*-specific Monoclonal Antibodies

Female Balb/C mice were immunized intraperitoneally with *B. burgdorferi* (DSM No. 5662). The first immunization was carried out with complete Freund's adjuvant, and 2–5 further immunizations with incomplete Freund's adjuvant followed at intervals of 2 weeks. 2 weeks later, the antigen was administered without adjuvant, and 3 days later the mice were sacrificed and the spleen was removed.

The spleen lymphocytes were mixed with mouse myeloma cells (Ag8-653) in the ratio 1:1, sedimented and mixed with fusion solution (2.5 g of polyethylene glycol (PEG), 2.5 ml of RPMI-medium, 250 μl of DMSO): 1 min addition of the fusion solution, incubation at 37° C. for 90 sec. The cells were again sedimented, the PEG was removed, and culture medium (HAT medium) was added. Finally, the cell suspension was inoculated into microtiter plates which contained macrophages as feeder cells and was incubated. Hybridoma supernatants were subjected undiluted to an indirect immunofluorescence assay (IFA) (Wilske, B.; Schierz, G.; Preac-Mursic, V.; Weber, K.; Pfister, H.-W.; Einhäupl, K. (1984): Sero-logical diagnosis of Erythema migrans disease and related disorders. Infection, 12, 331–337).

IFA-positive cell supernatants were subjected to Western blot analysis. Hybridomas which reacted in the Western blot were subcloned 4 times by limiting dilution, and their immunoglobulin class and IgG sub-class were identified.

The following monoclonal antibodies (MAB) were obtained in this way:

1. MAB against p41:
   (a) L41 1c11
      This antibody reacted with all 30 assayed *B. burgdorferi* strains and with Borrelia of relapsing fever (apart from *B. hermsii*) but not with Treponema.
   (b) L41 1D3
      This antibody reacted with the majority (21 of 24) of the *B. burgdorferi* strains but not with the Borrelia of relapsing fever and Treponema.
2. MAB against p100 (L100 1D4):
   This antibody reacted with all 30 assayed *B. burgdorferi* strains but not with the Borrelia of relapsing fever or Treponema.
3. MAB against pC (L22 1F8):
   This MAB reacted with pC proteins from strains from skin and CSF strains, whereas the pC proteins of some but not all tick strains were negative.
4. MAB against OspA:
   OspA is a major protein (30 kD region) of the outer membrane of most *B. burgdorferi* strains. OspA proteins of European *B. burgdorferi* strains are antigenetically heterogeneous and differ antigenetically from the American strains. The few OspA-negative strains have pC proteins.
   (a) L32 2E7
      In total, 29 of 32 strains reacted. The negative strains had no OspA protein. The 3 negative strains reacted with the pC-specific MAB L22 1F8.
   (b) L32 1G3:
      This MAB reacted with only 3 of 25 assayed strains.
The combination of MAB L32 2E7 and MAB L22 1F8 and the reaction with MAB L100 1D4 allows identification of *B. burgdorferi* Borrelia and Treponema. Reliable identification and differentiation of *B. burgdorferi* has not been possible with monoclonal antibodies available to date.

EXAMPLE 7

Determination of the Amino-acid Sequence of a Protein with a Molecular Weight of About 22 kD from Another Strain The amino-acid sequence of a protein with a molecular weight of about 22 kD was determined by the methods described in the previous examples. This protein was cloned from another Borrelia strain and was subsequently sequenced. This strain has been deposited at the ATCC under the number 35210 and is generally accessible. The following amino-acid sequence was determined in this case: (SEQ ID NO: 15)

Met Lys Lys Asn Thr Leu Ser Ala Ile Leu Met Thr Leu
Phe Leu Phe Ile Ser Cys Asn Asn Ser Gly Lys Asp Gly
Asn Thr Ser Ala Asn Ser Ala Asp Glu Ser Val Lys Gly
Pro Asn Leu Thr Glu Ile Ser Lys Lys Ile Thr Asp Ser
Asn Ala Val Leu Leu Ala Val Lys Glu Val Glu Ala Leu
Leu Ser Ser Ile Asp Glu Ile Ala Ala Lys Ala Ile Gly Lys
Lys Ile His Gln Asn Asn Gly Leu Asp Thr Glu Asn Asn
His Asn Gly Ser Leu Leu Ala Gly Ala Tyr Ala Ile Ser
Thr Leu Ile Lys Gln Lys Leu Asp Gly Leu Lys Asn Glu
Gly Leu Lys Glu Lys Ile Asp Ala Ala Lys Lys Cys Ser
Glu Thr Phe Thr Asn Lys Leu Lys Glu Lys His Thr Asp
Leu Gly Lys Glu Gly Val Thr Asp Ala Asp Ala Lys Glu
Ala Ile Leu Lys Thr Asn Gly Thr Lys Thr Lys Gly Ala
Glu Glu Leu Gly Lys Leu Phe Glu Ser Val Glu Val Leu
Ser Lys Ala Ala Lys Glu Met Leu Ala Asn Ser Val Lys
Glu Leu Thr Ser Pro Val Val Ala Glu Ser Pro Lys Lys
Pro

Amino-acid Sequence of pC Protein

EXAMPLE 8

Comparison of Assay Kits with Proteins According to the Invention and Those in Which an Ultrasonicate was Used 74 sera from patients with Erythema migrans were assayed for IgM and IgG antibodies. In addition, a negative control group of 100 blood donors was tested. In these assays, on the one hand ultrasonicate preparations of *Borrelia burgdorferi* were employed in accordance with methods known per se for carrying out ELISA assays. On the other hand, recombinant proteins prepared according to the invention were employed separately and together. The following tables show unambiguously that a considerably higher sensitivity can be achieved by the method according to the invention than when ultrasonicate is used.

| ELISA/antigen | Erythema migrans (n = 74) | |
|---|---|---|
| DETECTION of IgM antibodies | | |
| Ultrasonicate | 20 | 27.0% |
| p41 (recomb.) | 22 | 29.7% |
| OspA (recomb.) | 7 | 9.4% |
| pC (recomb.) | 26 | 35.1% |
| p41 and/or pC | 34 | 45.9% |
| p41 and/or pC and/or OspA | 34 | 45.9% |
| DETECTION of IgG antibodies | | |
| Ultrasonicate | 17 | 22.9% |
| p41 (recomb.) | 23 | 31.1% |
| OspA (recomb.) | 6 | 8.1% |
| pC (recomb.) | 27 | 36.5% |
| p41 and/or pC | 34 | 45.9% |
| p41 and/or pC and/or OspA | 35 | 47.3% |

-continued

| ELISA/antigen | Erythema migrans (n = 74) | |
|---|---|---|
| DETECTION of IgG and/or IgM antibodies | | |
| Ultrasonicate | 30 | 40% |
| p41 (recomb.) | 39 | 53% |
| OspA (recomb.) | 11 | 15% |
| pC (recomb.) | 41 | 55% |
| p41 and/or pC | 53 | 72% |
| p41 and/or pC and/or OspA | 53 | 72% |

Description of the Tables

Tab. 1
Reactivity of Lyme Borreliosis Sera from Various Stages of the Disease with *B. burgdorferi* Antigens (p17, pC, p41, p100) in Western Blot with *B. burgdorferi* Lysate as Antigen.

Table 1 summarizes the immunodominant proteins in various stages of Lyme borreliosis.

1.1. Sera from healthy people and, to a greater extent, from syphilis patients exhibited antibodies against p60 (common antigen). Antibodies against p41 were found less commonly.

1.2. For early manifestations (EM and LMR), the immunodominant proteins proved to be the flagella protein p41 and the pC protein. pC is the immunodominant protein for the early immune response. In particular, IgM antibodies against pC may occur earlier than IgM antibodies against p41 (see also FIG. 2a)

1.3. Sera from patients with late manifestations (ACA and arthritis) reacted in all cases (n=22) with p41 or p100 and in 21 cases with p100 or p17. p17 reacted in 17, p100 in 19 and p41 in 20 cases.

1.4. The intrathecal IgG immune response was directed against p41 in all 12 tested cases. Antibodies against p41 were undetectable in serum in 3 cases.

Tab. 2
Reactivity of the Immune Sera (Against Various Bacterial Pathogens) with Proteins from *B. burgdorferi* (Western Blot).

Western blot strips with *B. burgdorferi* lysate fractionated by electrophoresis were prepared as described in Example 1 and incubated with sera against various more or less related and therefore cross-reacting pathogens. The sera were derived from rabbits which had been immunized with the particular pathogens. p100 has the lowest cross-reactivity; only one (anti-*B. hermsii*) of the 15 assayed pathogen-specific sera reacts with this protein. p41 and pC each react with three of the sera and therefore also appear suitable for diagnostic use. The presence of immunoconserved antigens is distinctly evident; thus, for example, 14 and 12, respectively, of the assayed sera react with proteins 40 and 60 kD in size (p40; p60). These common antigens are therefore unsuitable for diagnostic use.

TABLE 1

Immunodominant proteins for the humoral immune response in Lyme borreliosis 1.1 Reactivity of human control sera (IgG Western blot)

| | pC | p41 | p60 | Number |
|---|---|---|---|---|
| Healthy | — | 2 | 3 | 17 |
| Syphilis | — | 1 | 5 | 9 |

1.2. Immune response to pC and p41 when there is Erythema migrans (EM) and lymphocytic meningoradiculitis (LMR) (Western blot)

| | Reactive proteins | | | |
|---|---|---|---|---|
| Diagnosis | p41 | pC | Ig class | Number |
| EM | 11 | 13 | IgM | 15[1] |
| LMR | 13 | 10 | IgM | 20[1] |
| | 14 | 3 | IgG | 15[2] |

1.3. Immune response to p100, p41 and p17 (IgG Western blot)

| Diagnosis | p100 | p41 | p17 | p100 or p41 | p100 or p17 | Number |
|---|---|---|---|---|---|---|
| ACA | 8 | 8 | 9 | 10 | 10 | 10 |
| Arthritis | 11 | 12 | 8 | 12 | 11 | 12 |

1.4. Intrathecal immune response when there is lymphocytic meningoradiculitis (IgG Western Blot)

| | Local intrathecal immune response | Reactivity in serum | Number |
|---|---|---|---|
| p41 | 12 | 9 | 12 |
| other proteins | 7 | 12 | 12 |

[1] The sera were positive in the IgM IFA AB assay.
[2] The sera were positive in the IgG IFA AB assay.

TABLE 2

Reactivity of immune sera (against various bacterial pathogens) with proteins from *B. burgdorferi* (Western blot)

| Protein | B. hermsii | T. phagedenis | T. pallidum | L. grippotyphosa | C. jejuni | E. coli | S. typhimurium | Sh. flexneri | Y. enterocolitica 03 |
|---|---|---|---|---|---|---|---|---|---|
| p100 | + | − | − | − | − | − | − | − | − |
| p75 | + | + | − | + | + | + | + | + | + |
| p70 | − | + | + | − | + | − | − | + | + |

TABLE 2-continued

Reactivity of immune sera (against various bacterial pathogens) with proteins from B. burgdorferi (Western blot)

|  |  |  |  |  |  |  |  |  |  |
|---|---|---|---|---|---|---|---|---|---|
| p60 | + | + | − | + | + | + | + | + | + |
| p41 | + | + | − | + | − | − | − | − | − |
| p40 | + | + | + | + | + | + | + | + | + |
| OspB | + | + | + | − | + | + | − | + | + |
| p33 | + | + | + | − | + | + | + | − | + |
| OspA | − | − | − | − | − | − | − | − | − |
| p30 | + | + | − | − | − | + | − | − | + |
| p23 | + | + | − | − | − | + | + | + | + |
| pC | + | − | − | − | − | − | − | + | − |
| p21 | − | + | − | − | − | − | + | + | + |

| Protein | Y. enterocolitica 09 | P. aeruginosa | H. influenzae | N. meningitidis | L. monocytogenes 01 | L. micdadei | Σ |
|---|---|---|---|---|---|---|---|
| p100 | − | − | − | − | − | − | 1 |
| p75 | + | + | + | − | + | − | 12 |
| p70 | + | + | + | − | + | + | 10 |
| p60 | + | + | + | + | − | − | 12 |
| p41 | − | − | − | − | − | − | 3 |
| p40 | + | + | + | + | + | − | 14 |
| OspB | − | − | + | − | − | + | 9 |
| p33 | + | + | + | + | + | − | 12 |
| OspA | − | − | − | − | − | − | 0 |
| p30 | − | − | − | − | + | − | 5 |
| p23 | + | + | − | − | − | − | 8 |
| pC | + | − | − | − | − | − | 3 |
| p21 | + | + | − | − | − | − | 6 |

DESCRIPTION OF THE FIGURES

FIG. 1:

Figure 2A:
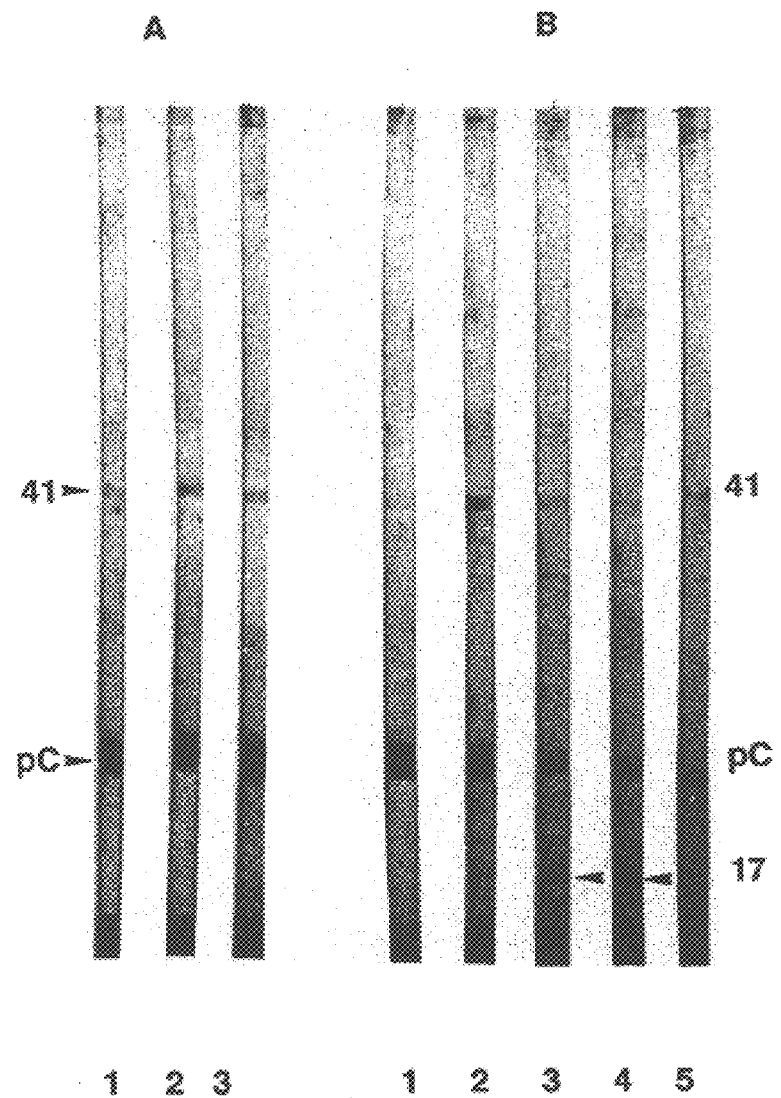
Figure 2B:
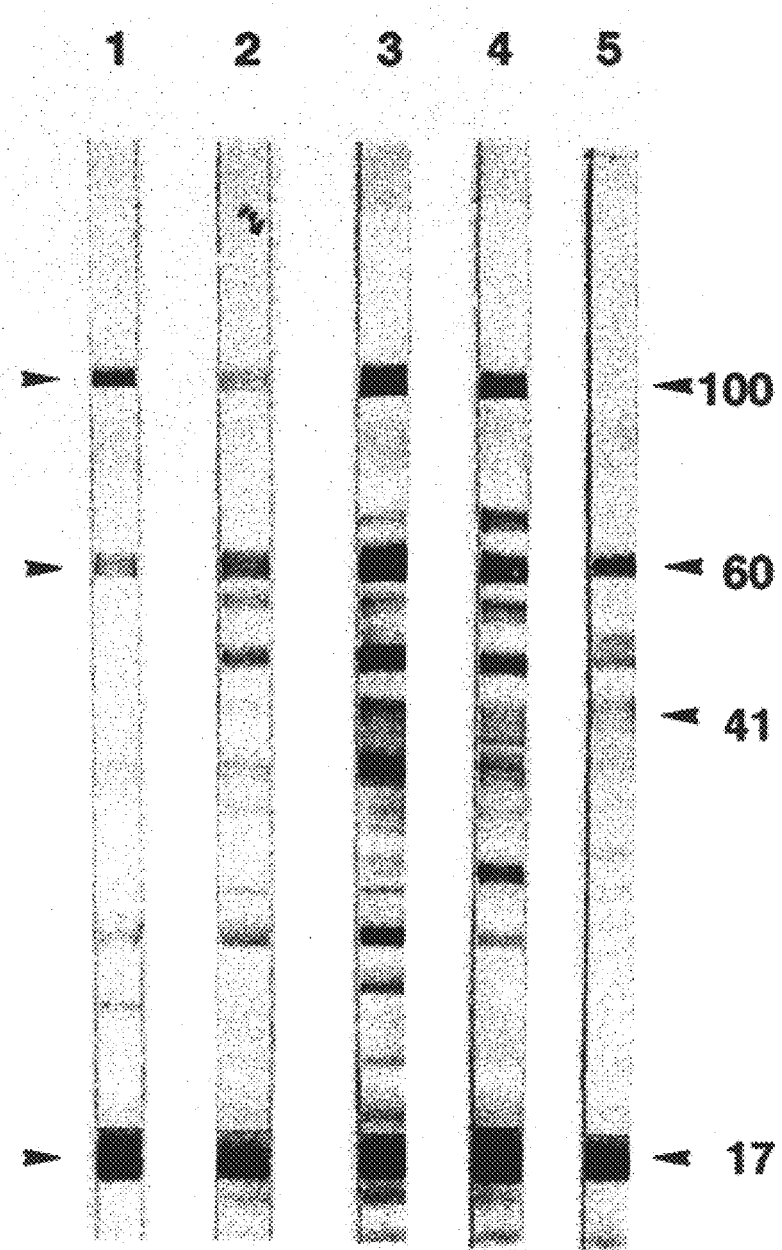
Figure 3:
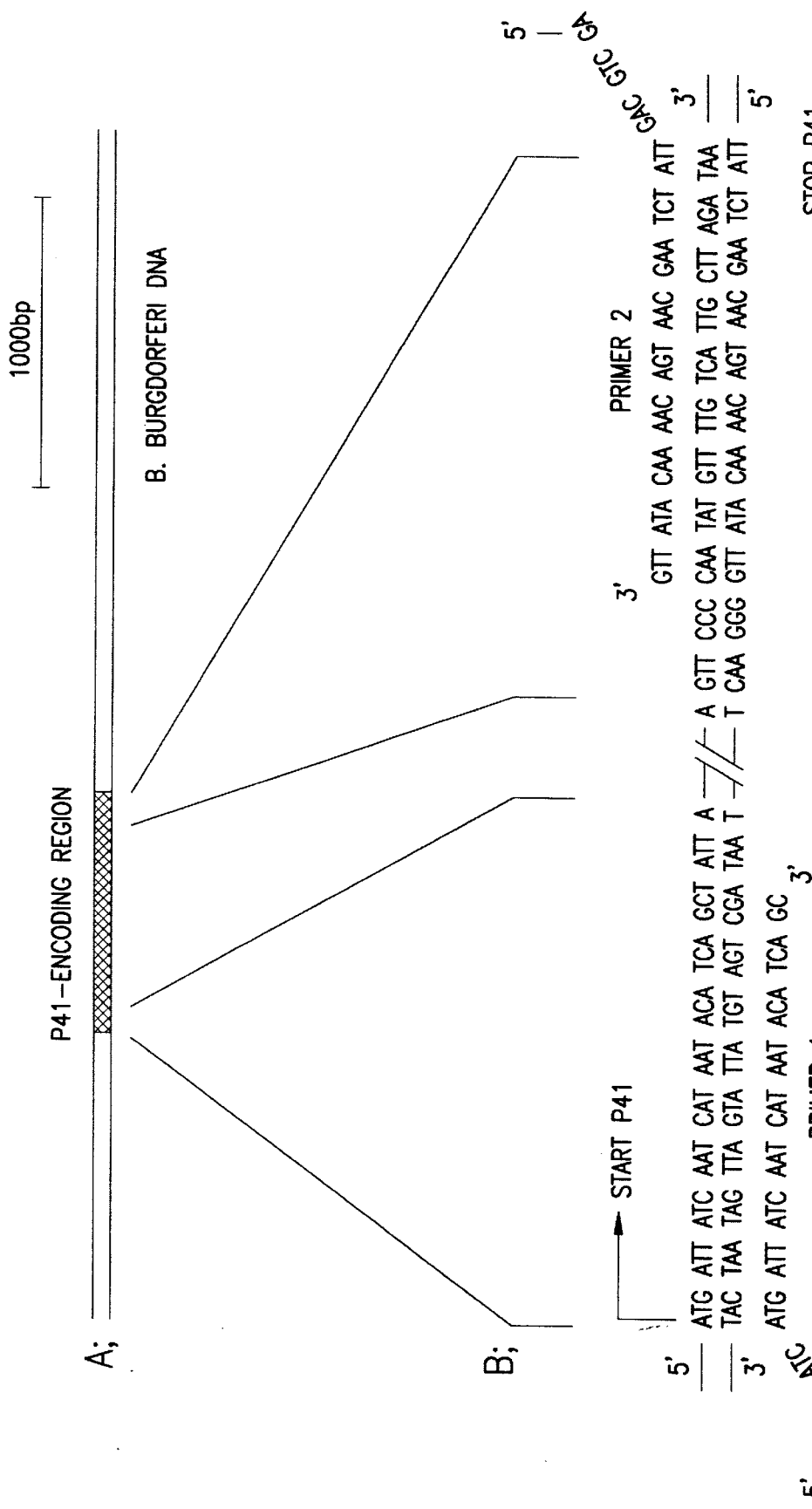

Reactivity of B. burgdorferi-infected Patients with Lysates from 5 Different B. burgdorferi Strains in a Western Blot.

Sera from stages II and III (neuroborreliosis, stage II (IgM and IgG); acrodermatitis (IgG) and arthritis (IgG), stage III) were assayed. The early immune response is directed, irrespective of the assayed strain, against a narrow spectrum of Borrelia proteins (pC and p41). The late immune response is directed against a broad panel of Borrelia proteins. Immunodominant proteins are (irrespective of the assayed strain) p100 (with variable molecular weight) and p41.

FIG. 2A and 2B

2a) Monitoring Progress (IgM Western Blot) of Erythema Migrans

The pC protein may be the immunodominant protein of the early immune response. Antibodies against p41 may occur later and be expressed only weakly. IgM antibodies against p17 may also occur when the disease has lasted a long time.

2b) IgG Western Blot When There are Late Manifestations

IgG antibodies recognize a broad spectrum of Borrelia proteins. The immunodominant proteins when the PKo strain is used prove to be p17 and p100. p17 is strongly expressed by the PKo strain (in contrast to other strains; see FIG. 1). The flagellin p41 was not recognized in 2 of these examples (serum 1 and 2).

FIG. 3

Diagram of DNA Amplification of the p41-Encoding Region

A;

Section of the B. burgdorferi DNA with the p41-encoding region (black bar). B; Enlargement of the 5' or 3' end of the p41 gene with the relevant DNA sequences. Also indicated is the translation start (ATG) and the stop codon at the 3' end (TAA). The primer sequences used for the PCR are additionally indicated below (primer 1) and above (primer 2) the p41-encoding DNA double-strand. The primers can be hybridized only with the 3' regions in each case. The 5' ends contain non-hybridizing parts which represent cleavage sites for restriction enzymes: GGATCC-BamHI; TCATGA-BspHI, at the 5' end; GACGTC-PstI at the 3' end.

FIG. 4

Expression, Reactivity and Purification of Recombinant p41.

Left side: Coomassie blue-stained SDS polyacrylamide gel. The individual lanes were loaded as follows: 1, E. coli lysate, negative control; 2, E. coli lysate with pUC8ly17 after IPTG induction, the p41 produced by recombination is evident as additional bands in the region of about 45 kDa; 3, supernatant of the lysate from 2 after disruption of the cells as described in Example 4; 4, pellet fraction of the lyzed cells with the recombinant p41; 5, octyl glucopyranoside supernatant; 6, as 5 but pellet fractions; 7–10, fractions after elution of p41 from a MonoQ column by a salt gradient; lanes 9 and 10 contain recombinant p41, owing to degradation events and incomplete translation, besides the complete product there are also smaller fragments which, however, are also to be found in authentic p41 material from B. burgdorferi.

Right side: immunostained Western blot of an SDS gel with samples of the Coomassie-stained gel. The immunostaining was carried out with a monoclonal antibody described in Example 6. Labeling of the lanes and of the samples as Coomassie-stained gel; lane 0, empty lane.

FIG. 5

HPLC Elution Profile of p41 from an ion Exchanger Column with a Salt Gradient.

Figure 4:
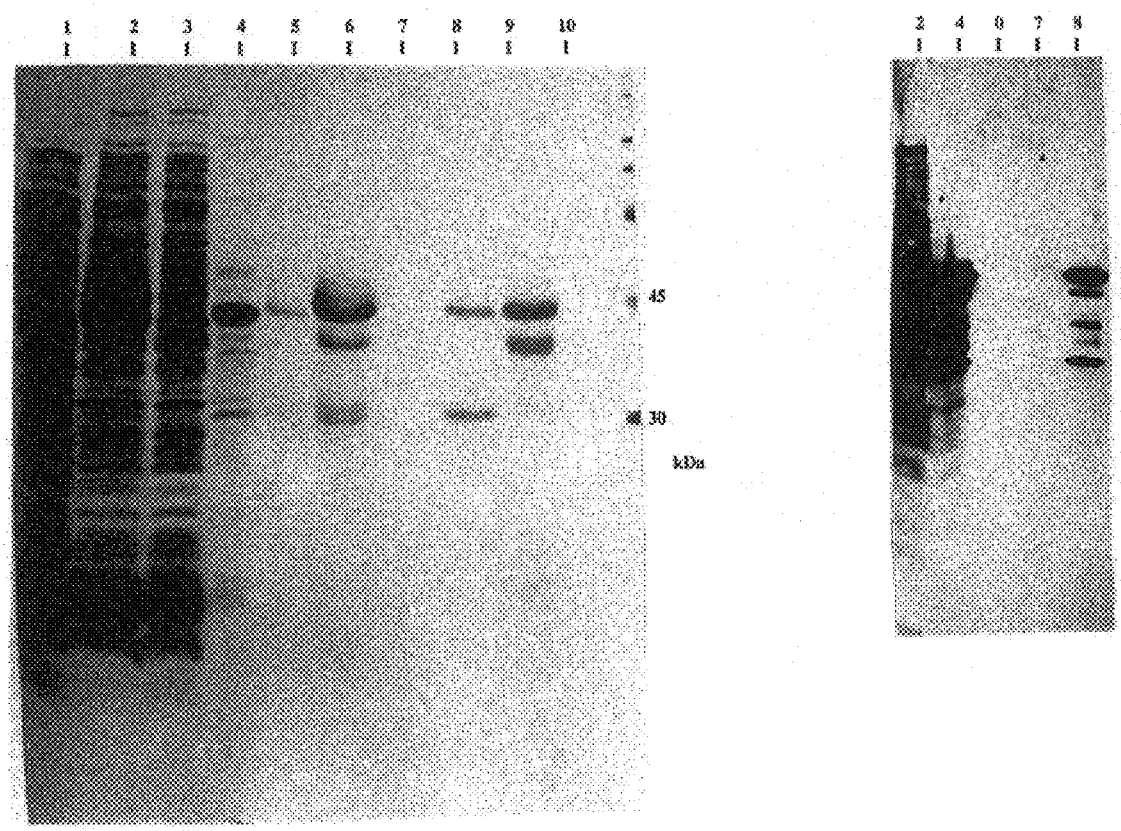

The anion exchanger purification (MonoQ from Pharmacia) of p41 was followed by the antigen being back-dialyzed against 4 M urea without salt and again loaded onto the MonoQ column to check the purity. The elution profile now shows only one protein adsorption peak. The smaller peak immediately in front of the main fraction corresponds to the p41 fragment, with a size of about 30 kD, visible in FIG. 4., lane 8 (assayed by Western blot).

FIG. 6:

IgG ELISA with Recombinant p41 as Antigen.

Figure 5:
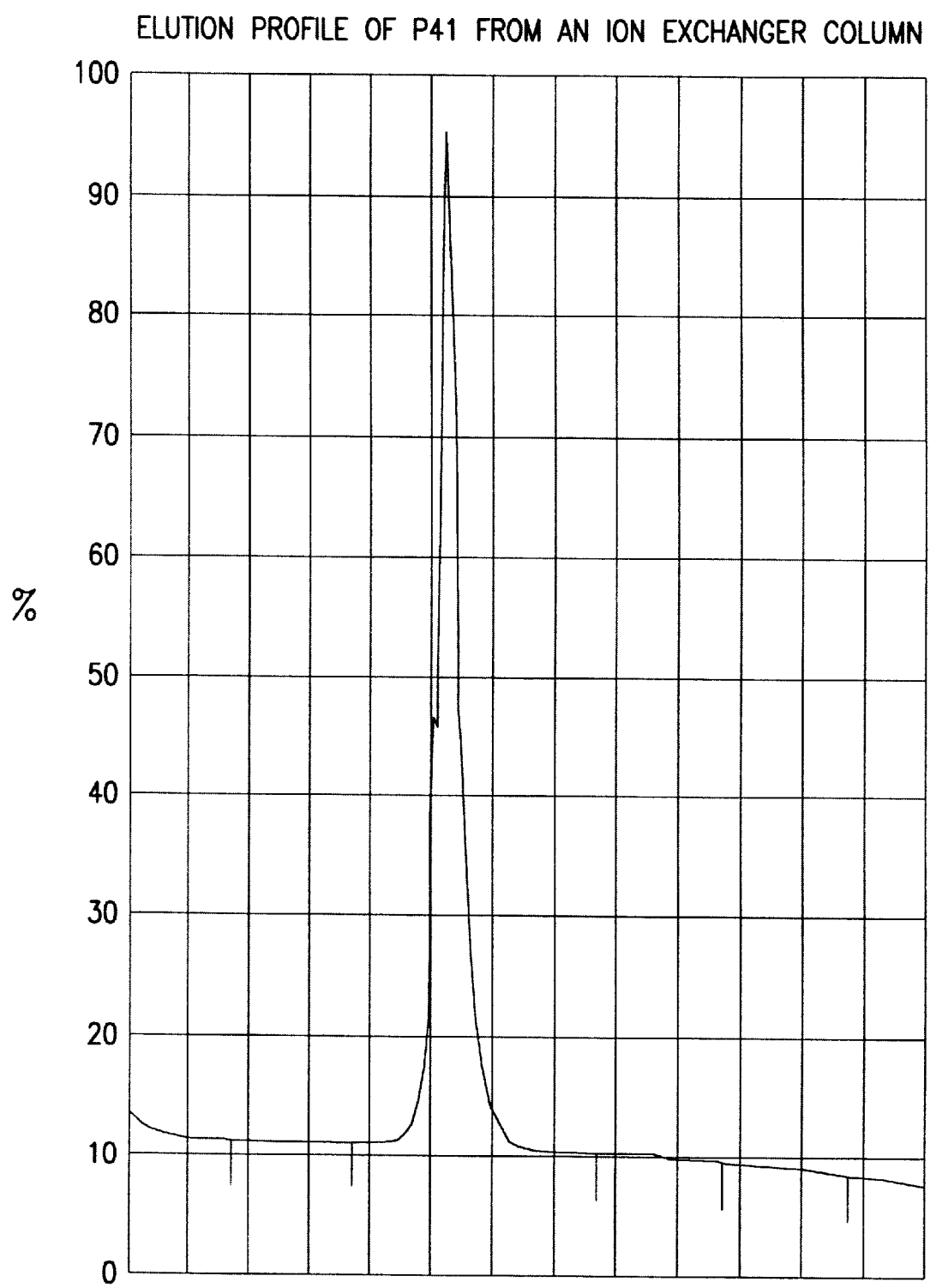
Figure 6:
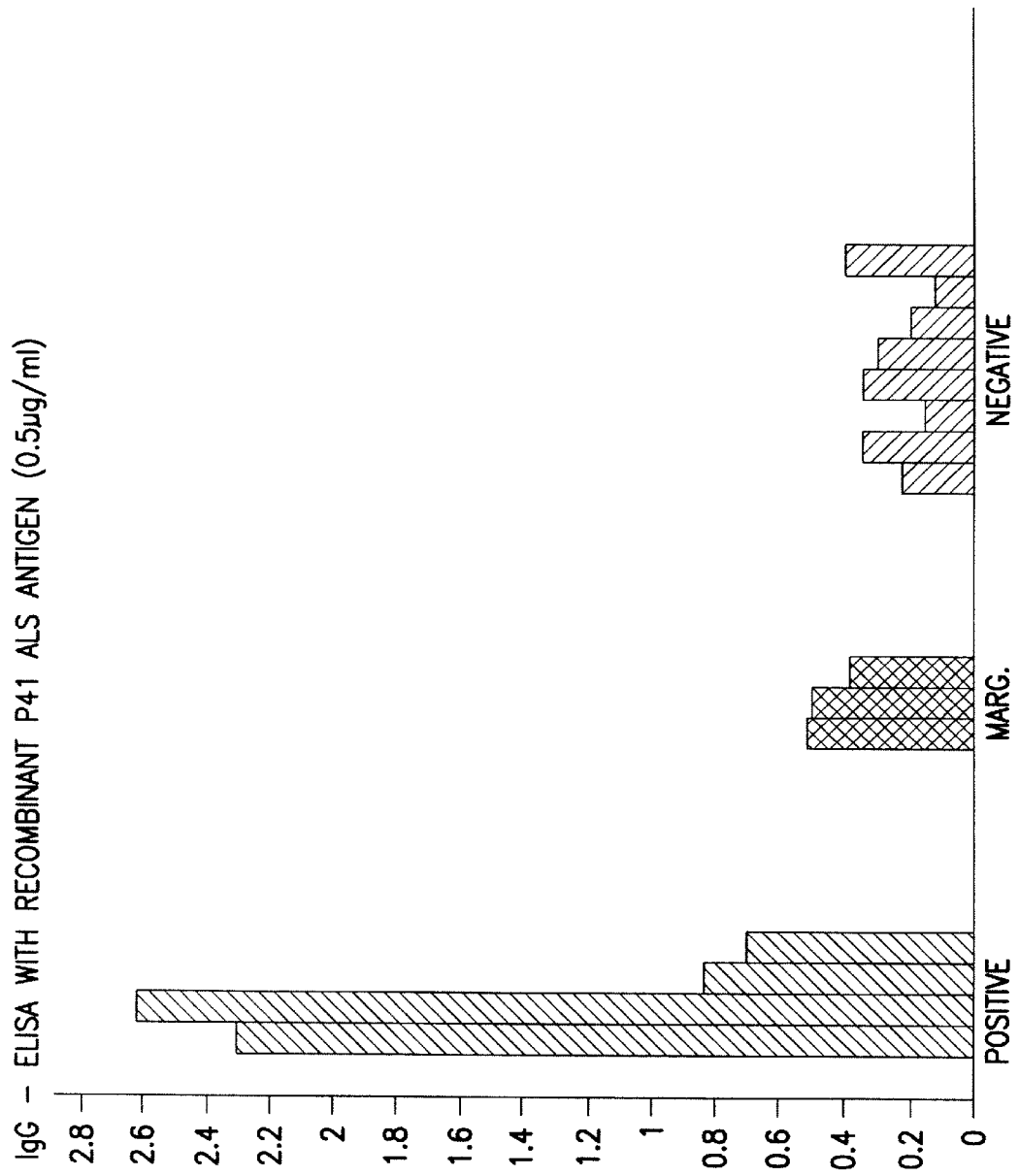
Figure 7B:
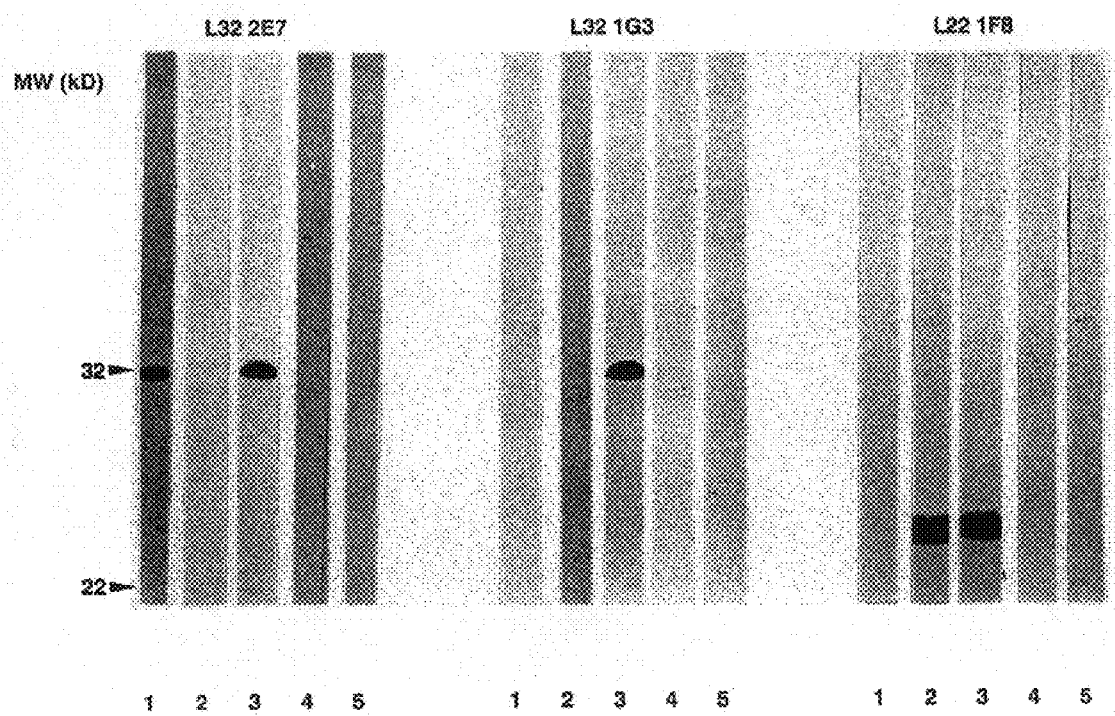

The recombinant antigen purified on an anion exchanger (MonoQ) (see FIG. 5) was employed in a concentration of 0.5 µg/ml. 7 sera from patients with clinically defined Lyme borreliosis and 8 sera from healthy subjects were assayed. 4 sera from the Lyme borreliosis patients reacted strongly in the Western blot with the recombinant p41 (=positive), 3 sera reacted weakly (=marginal), while sera from the healthy subjects did not react (=negative). The IgG ELISA showed a comparable result. Y axis: optical density at wavelength 486 nm; marg. marginal

FIG. 7A and 7B

Reactivity of Monoclonal Antibodies Against Various *B. burgdorferi* Antigens.

Six monoclonal bodies against *B. burgdorferi* were assayed with 30 different *B. burgdorferi* strains, 4 relapsing fever Borrelia strains and 2 different Treponema. The figure depicts as examples three different *B. burgdorferi* isolates (1=B31, American strain; 2=PKo, German skin strain; 3=PBi, German CSF strain), one relapsing fever Borrelia (4=*B. hermsii*) and one Treponema strain (5=*T. phagedenis*). The monoclonal antibodies prepared as in Example 6 were employed.

What is claimed is:

1. A purified protein obtained from *Borrelia burgdorferi* wherein the protein is characterized in that it
   a. elicits an immunological response against *Borrelia burgdorferi* from a mammal;
   b. has been prepared by expression in a bacterium other than *Borrelia burgdorferi;*
   c. is free of other proteins derived from *Borrelia burgdorferi*; and
   d. is a protein comprising SEQ ID NO: 5 or is a protein consisting of at least 10 amino acids of SEQ ID NO: 5.

2. The purified protein of claim 1 which is prepared using DNA isolated from *Borrelia burgdorferi*.

3. The purified protein of claim 2 which is prepared using DNA isolated from *Borrelia burgdorferi* (DSM No. 5662).

4. A composition comprising an amount of an isolated immunologically active protein comprising SEQ ID NO: 5 or is an isolated protein consisting of at least 10 amino acids of SEQ ID NO: 5, and a pharmaceutically acceptable carrier, which amount is effective to stimulate the formation of antibodies against *Borrelia burgdorferi* in a person.

5. The composition of claim 4 which further comprises an effective amount of an immune stimulating agent.

* * * * *